(12) United States Patent
Kamal et al.

(10) Patent No.: US 8,916,711 B2
(45) Date of Patent: Dec. 23, 2014

(54) IMIDAZOTHIAZOLE-CHALCONE DERIVATIVES AS POTENTIAL ANTICANCER AGENTS AND PROCESS FOR THE PREPARATION THEREOF

(75) Inventors: Ahmed Kamal, Hyderabad (IN); Dastagiri Dudekula, Hyderabad (IN); Surendranadha Reddy Jonnala, Hyderabad (IN); Vijaya Bharathi Earla, Hyderabad (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 13/502,944

(22) PCT Filed: Oct. 7, 2010

(86) PCT No.: PCT/IB2010/002544
§ 371 (c)(1),
(2), (4) Date: Jul. 12, 2012

(87) PCT Pub. No.: WO2011/045646
PCT Pub. Date: Apr. 21, 2011

(65) Prior Publication Data
US 2012/0271054 A1    Oct. 25, 2012

(30) Foreign Application Priority Data
Oct. 13, 2009    (IN) .......................... 2121/DEL/2009

(51) Int. Cl.
*C07D 513/04* (2006.01)
(52) U.S. Cl.
CPC .................................... *C07D 513/04* (2013.01)
USPC ........................................ 546/270.1; 548/154
(58) Field of Classification Search
None
See application file for complete search history.

(56) References Cited

FOREIGN PATENT DOCUMENTS

WO    WO 0179187 A2 *    10/2001

* cited by examiner

*Primary Examiner* — Zinna Northington Davis
(74) *Attorney, Agent, or Firm* — Lowe Hauptman & Ham, LLP

(57) ABSTRACT

The present invention provides a compounds 7a-f to 18a-f and 19a-f to 30a-f of general formula A, useful as potential anticancer agents against human cancer cell lines. The present invention further provides a process for the preparation of imidazothiazole-chalcone hybrids 7a-f to 18a-f and 19a-f to 30a-f of general formula A

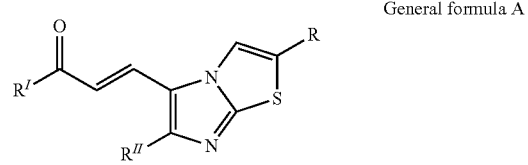

General formula A wherein R = H for 7a-f to 18a-f
R = CH₃ for 19a-f to 30a-f

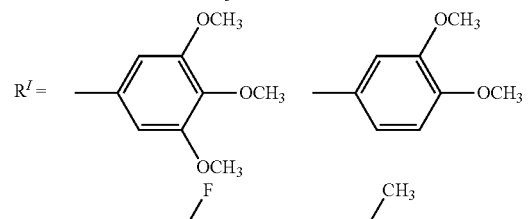

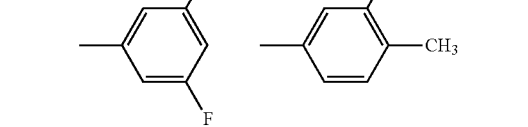

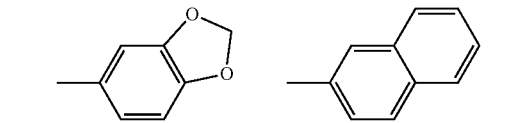

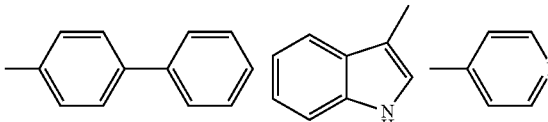

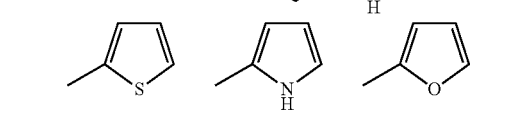

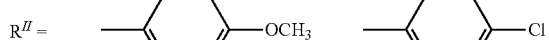

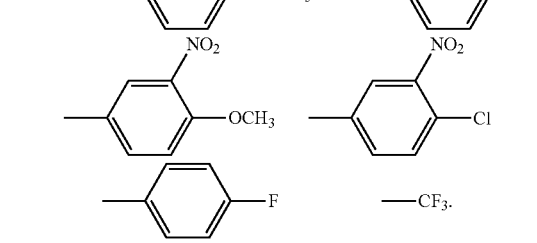

14 Claims, 2 Drawing Sheets

5 wherein

R = H, CH₃

R'' =

6 wherein

R' =

IMIDAZOTHIAZOLE-CHALCONE DERIVATIVES AS POTENTIAL ANTICANCER AGENTS AND PROCESS FOR THE PREPARATION THEREOF

RELATED APPLICATIONS

The present application is a National Phase of International Application Number PCT/IB2010/002544, filed Oct. 7, 2010, and claims priority from, Indian Application Number 2121/DEL/2009, filed Oct. 13, 2009.

The following specification particularly describes the invention and the manner in which it is to be performed:

FIELD OF THE INVENTION

The present invention relates to novel imidazothiazole-chalcone derivatives of general formula A.

General formula A wherein

R = H for 7a-f to 18a-f
R = $CH_3$ for 19a-f to 30a-f $R^I$ =

$R^{II}$ =

The present invention also relates to the process of preparation of imidazothiazole-chalcone hybrids of general formula A.

The present invention also relates to (E)-3-(6-(4-methoxyphenyl)imidazo[2,1-b]thiazol-5-yl)-1-(3,4,5-trimethoxyphenyl)prop-2-en-1-one (7a), (E)-3-(6-(4-fluorophenyl)imidazo[2,1-b]thiazol-5-yl)-1-(3,4,5-trimethoxyphenyl) prop-2-en-1-one (7e), (E)-3-(6-(trifluoromethyl)imidazo[2,1-b]thiazol-5-yl)-1-(3,4,5-trimethoxyphenyl)prop-2-en-1-one (7f), (E)-1-(3,4-dimethoxyphenyl)-3-(6-(trifluoromethyl)imidazo[2,1-b]thiazol-5-yl) prop-2-en-1-one (8f) and (E)-3-(6-(4-fluorophenyl)-2-methylimidazo[2,1-b]thiazol-5-yl)-1-(3,4,5-trimethoxyphenyl)prop-2-en-1-one (19e); useful as anticancer agents.

BACKGROUND OF THE INVENTION AND PRIOR ART

Many clinically successful anticancer drugs acting as antimitotics interfere with dynamic instability of microtubules; spindle poisons arrest-dividing cells in G2/M phase of the cell cycle, causing apoptotic cell death. Among the natural products affecting microtubule dynamic are colchicines, the vinca alkaloids, combretastatin A4, epothilane, and taxanes. Chalcones are the flavone precursors that possess the antimitotic activity and possess greater antiproliferative activity. Michael L. Edwards, David M. Stemerick, Prasad S. Sunkara, *J. Med. Chem.*, 1990, 33 (7), 1948-1954. Ahcène Boumendjel,*, Julien Boccard, Pierre-Alain Carrupt, Edwige Nicolle, Madeleine Blanc, *J. Med. Chem.* 2008, 51, 2307-2310. The anticancer activity of 3-(5-imidazo[2,1-b]thiazolylmethylene)-2-indolinones have been reported in 1997. Similarly the new guanylhydrazones from imidazo[2,1-b]thiazoles have shown promising anticancer activity. Aldo Andreani,*, Silvia Burnelli, Massimiliano Granaiola, Alberto Leoni, Alessandra Locatelli *J. Med. Chem.* 2008, 51, 809-816, Aldo Andreani,*, Silvia Burnelli, Massimiliano Granaiola, Alberto Leoni, Alessandra Locatelli, *J. Med. Chem.* 2007, 50, 3167-3172, Aldo Andreani,*, Massimiliano Granaiola, Alberto Leoni, Alessandra Locatelli, Rita Morigi, *J. Med. Chem.* 2005, 48, 3085-3089. Moreover the activity of chalcones was found to be dependent on both A and B rings. Hence some new hybrids were prepared by replacing the B ring in chalcone with imidazothiazole moiety, which is already well known for their antitumor activity. These hybrids have shown potent cytotoxicity in the NCI cell line screen for evaluation of their anticancer activity.

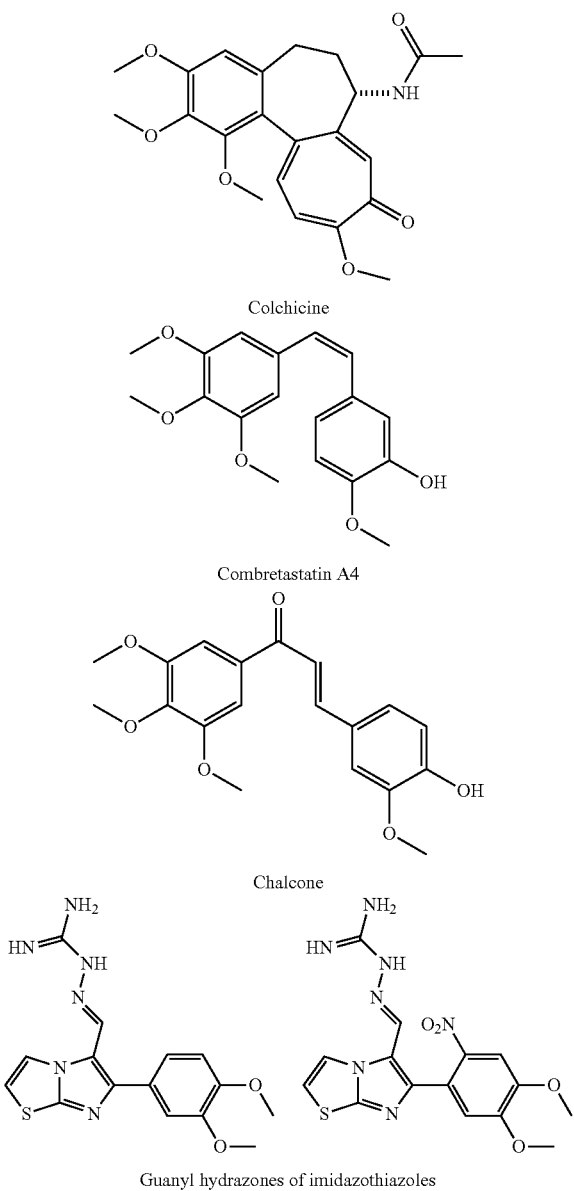

Colchicine

Combretastatin A4

Chalcone

Guanyl hydrazones of imidazothiazoles

OBJECTIVES OF THE INVENTION

The main objective of the present invention is to provide novel Imidazothiazole-chalcone hybrids of general formula A.

Another objective of the present invention is to provide novel Imidazothiazole-chalcone hybrids of general formula A, useful as anticancer agents.

Yet another objective of the present invention is to provide a process for the preparation of Imidazothiazole-chalcone hybrids of general formula A.

SUMMARY OF THE INVENTION

Accordingly, the present invention provides Imidazothiazole-chalcone hybrids of general formula A

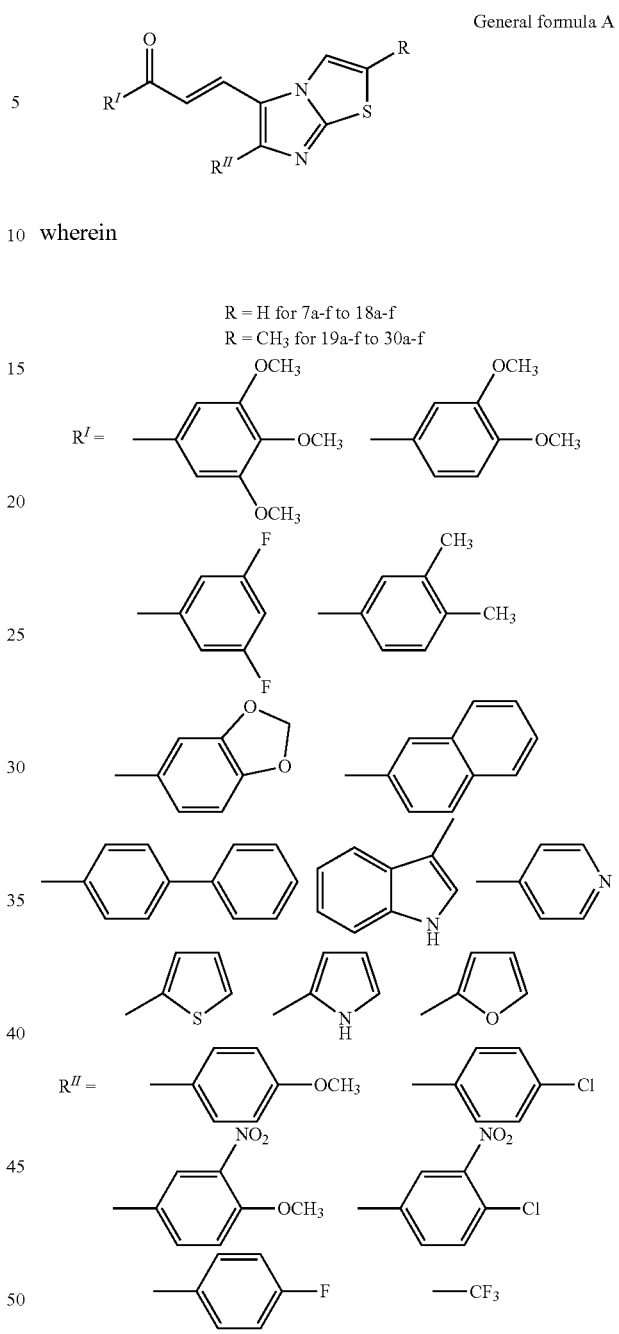

General formula A wherein

R = H for 7a-f to 18a-f
R = CH₃ for 19a-f to 30a-f

In an embodiment, the present invention provides compounds of general formula A represent as follow:

(7a) (E)-3-(6-(4-methoxyphenyl)imidazo[2,1-b]thiazol-5-yl)-1-(3,4,5-trimethoxyphenyl) prop-2-en-1-one
(E)-3-(6-(4-methoxyphenyl)imidazo[2,1-b]thiazol-5-yl)-1-(3,4,5-trimethoxyphenyl) prop-2-en-1-one; (7a)
(E)-3-(6-(4-chlorophenyl)imidazo[2,1-b]thiazol-5-yl)-1-(3,4,5-trimethoxyphenyl)prop-2-en-1-one; (7b)
(E)-3-(6-(4-methoxy-3-nitrophenyl)imidazo[2,1-b]thiazol-5-yl)-1-(3,4,5-trimethoxy-phenyl)prop-2-en-1-one; (7c)
(E)-3-(6-(4-chloro-3-nitrophenyl)imidazo[2,1-b]thiazol-5-yl)-1-(3,4,5-trimethoxy-phenyl)prop-2-en-1-one; (7d)
(E)-3-(6-(4-fluorophenyl)imidazo[2, 1-1)]thiazol-5-yl)-1-(3,4,5-trimethoxyphenyl)prop-2-en-1-one; (7e)

(E)-3-(6-(trifluoromethyl)imidazo[2, 1-1)]thiazol-5-yl)-1-(3,4,5-trimethoxyphenyl)prop-2-en-1-one; (7f)
(E)-3-(6-(4-methoxyphenyl)-2-methylimidazo[2, 1-1)]thiazol-5-yl)-1-(3,4,5-trimethoxyphenyl)prop-2-en-1-one; (19a)
(E)-3-(6-(4-chlorophenyl)-2-methylimidazo[2, 1-1)]thiazol-5-yl)-1-(3,4,5-trimethoxyphenyl)prop-2-en-1-one; (19b)
(E)-3-(6-(4-methoxy-3-nitrophenyl)-2-methylimidazo[2,1-b]thiazol-5-yl)-1-(3,4,5-trimethoxyphenyl)prop-2-en-1-one; (19c)
(E)-3-(6-(-(4-chloro-3-nitrophenyl)-2-methylimidazo[2,1-b]thiazol-5-yl)-1-(3,4,5-trimethoxyphenyl)prop-2-en-1-one; (19d)
(E)-3-(6-(4-fluorophenyl)-2-methylimidazo[2, 1-1)]thiazol-5-yl)-1-(3,4,5-trimethoxyphenyl)prop-2-en-1-one; (19e)
(E)-3-(2-methyl-6-(trifluoromethyl)imidazo[2,1-b]thiazol-5-yl)-1-(3,4,5-trimethoxyphenyl)prop-2-en-1-one; (19f)
(E)-1-(3,4-dimethoxyphenyl)-3-(6-(4-methoxyphenyl)imidazo[2,1-b]thiazol-5-yl)prop-2-en-1-one; (8a)
(E)-3-(6-(4-chlorophenyl)imidazo[2,1-b]thiazol-5-yl)-1-(3,4-dimethoxyphenyl) Prop-2-en-1-one; (8b)
(E)-1-(3,4-dimethoxyphenyl)-3-(6-(4-methoxy-3-nitrophenyl)imidazo[2,1-b]Thiazol-5-yl)prop-2-en-1-one; (8c)
(E)-3-(6-(4-chloro-3-nitrophenyl)imidazo[2,1-b]thiazol-5-yl)-1-(3,4-dimethoxy phenyl) prop-2-en-1-one; (8d)
(E)-1-(3,4-dimethoxyphenyl)-3-(6-(4-fluorophenyl)imidazo[2,1-b]thiazol-5-yl) Prop-2-en-1-one; (8e)
(E)-1-(3,4-dimethoxyphenyl)-3-(6-(trifluoromethyl)imidazo[2,1-b]thiazol-5-yl) Prop-2-en-1-one; (8f)
(E)-1-(3,4-dimethoxyphenyl)-3-(6-(4-methoxyphenyl)-2-methylimidazo[2,1-b]thiazol-5-yl)prop-2-en-1-one; (20a)
(E)-3-(6-(4-chlorophenyl)-2-methylimidazo[2,1-b]thiazol-5-yl)-1-(3,4-dimethoxy phenyl)prop-2-en-1-one; (20b)
(E)-1-(3,4-dimethoxyphenyl)-3-(6-(4-methoxy-3-nitrophenyl)-2-methylimidazo[2,1-b]thiazol-5-yl)prop-2-en-1-one; (20c)
(E)-3-(6-(4-chloro-3-nitrophenyl)-2-methylimidazo[2,1-b]thiazol-5-yl)-1-(3,4-dimethoxyphenyl)prop-2-en-1-one; (20d)
(E)-1-(3,4-dimethoxyphenyl)-3-(6-(4-fluorophenyl)-2-methylimidazo[2,1-b]thiazol-5-yl) prop-2-en-1-one; (20e)
(E)-1-(3,4-dimethoxyphenyl)-3-(2-methyl-6-(trifluoromethyl)imidazo[2,1-b]thiazol-5-yl)prop-2-en-1-one; (20f)
(E)-1-(3,4-dimethylphenyl)-3-(6-(4-methoxyphenyl)imidazo[2,1-b]thiazol-5-yl) prop-2-en-1-one; (9a)
(E)-3-(6-(4-chlorophenyl)imidazo[2,1-b]thiazol-5-yl)-1-(3, 4-dimethylphenyl) Prop-2-en-1-one; (9b)
(E)-1-(3,4-dimethylphenyl)-3-(6-(4-methoxy-3-nitrophenyl)imidazo[2,1-b]Thiazol-5-yl)prop-2-en-1-one; (9c)
(E)-3-(6-(4-chloro-3-nitrophenyl)imidazo[2,1-b]thiazol-5-yl)-1-(3,4-dimethyl phenyl)prop-2-en-1-one; (9d)
(E)-1-(3,4-dimethylphenyl)-3-(6-(4-fluorophenyl)imidazo[2,1-b]thiazol-5-yl) prop-2-en-1-one; (9e)
(E)-1-(3,4-dimethylphenyl)-3-(6-(trifluoromethyl)imidazo[2,1-b]thiazol-5-yl) prop-2-en-1-one; (9f)
(E)-1-(3,4-dimethylphenyl)-3-(6-(4-methoxyphenyl)-2-methylimidazo[2,1-b]thiazol-5-yl)prop-2-en-1-one; (21a)
(E)-3-(6-(4-chlorophenyl)-2-methylimidazo[2,1-b]thiazol-5-yl)-1-(3,4-dimethyl phenyl)prop-2-en-1-one; (21b)
(E)-1-(3,4-dimethylphenyl)-3-(6-(4-methoxy-3-nitrophenyl)-2-methylimidazo[2,1-b]thiazol-5-yl)prop-2-en-1-one; (21c)
(E)-3-(6-(4-chloro-3-nitrophenyl)-2-methylimidazo[2,1-b]thiazol-5-yl)-1-(3,4-dimethylphenyl)prop-2-en-1-one; (21d)
(E)-1-(3,4-dimethylphenyl)-3-(6-(4-fluorophenyl)-2-methylimidazo[2,1-b]thiazol-5-yl)prop-2-en-1-one; (21e)
(E)-1-(3,4-dimethylphenyl)-3-(2-methyl-6-(trifluoromethyl)imidazo[2,1-b]thiazol-5-yl)prop-2-en-1-one; (21f)
(E)-1-(3,5-d fluorophenyl)-3-(6-(4-methoxyphenyl)imidazo[2,1-b]thiazo-5-yl) prop-2-en-1-one; (10a)
(E)-3-(6-(4-chlorophenyl)imidazo[2,1-b]thiazol-5-yl)-1-(3, 5-difluorophenyl) prop-2-en-1-one; (10b)
(E)-1-(3,5-difluorophenyl)-3-(6-(4-methoxy-3-nitrophenyl)imidazo[2,1-b]thiazol-5-yl)prop-2-en-1-one; (10c)
(E)-3-(6-(4-chloro-3-nitrophenyl)imidazo[2,1-b]thiazol-5-yl)-1-(3,5-difluorophenyl)prop-2-en-1-one; (10d)
(E)-1-(3,5-difluorophenyl)-3-(6-(4-fluorophenyl)imidazo[2,1-h]thiazol-5-yl)prop-2-en-1-one; (10e)
(E)-1-(3,5-difluorophenyl)-3-(6-(trifluoromethyl)imidazo[2,1-b]thiazol-5-yl)prop-2-en-1-one; (10f)
(E)-1-(3,5-difluorophenyl)-3-(6-(4-methoxyphenyl)-2-methyl imidazo[2,1-b]thiazol-5-yl)prop-2-en-1-one; (22a)
(E)-3-(6-(4-chlorophenyl)-2-methylimidazo[2,1-b thiazol-5-yl)-1-(3,5-difluoro phenyl) prop-2-en-1-one; (22b)
(E)-1-(3,5-difluorophenyl)-3-(6-(4-methoxy-3-nitrophenyl)-2-methylimidazo[2, 1-1)]thiazol-5-yl)prop-2-en-1-one; (22c)
(E)-3-(6-(4-chloro-3-nitrophenyl)-2-methylimidazo[2,1-b]thiazol-5-yl)-1-(3,5-difluoro phenyl)prop-2-en-1-one; (22d)
(E)-1-(3,5-difluorophenyl)-3-(6-(4-fluorophenyl)-2-methylimidazo[2,1-b]thiazol-5-yl)prop-2-en-1-one; (22e)
(E)-1-(3,5-difluorophenyl)-3-(2-methyl-6-(trifluoromethyl)imidazo[2,1-b]thiazol-5-yl)prop-2-en-1-one; (22f)
(E)-1-(benzo[d][1,3]dioxol-5-yl)-3-(6-(4-methoxyphenyl)imidazo[2,1-b]thiazol-5-yl)prop-2-en-1-one; (11a)
(E)-1-(benzo[d][1,3]dioxol-5-yl)-3-(6-(4-chlorophenyl)imidazo[2,1-b]thiazol-5-yl)prop-2-en-1-one; (11b)
(E)-1-(benzo[d][1,3]dioxol-5-yl)-3-(6-(4-methoxy-3-nitrophenyl)imidazo[2,1-b]thiazol-5-yl)prop-2-en-1-one; (11c)
(E)-1-(benzo[d][1,3]dioxol-5-yl)-3-(6-(4-chloro-3-nitrophenyl)imidazo[2,1-b]thiazol-5-yl)prop-2-en-1-one; (11d)
(E)-1-(benzo[d][1,3]dioxol-5-yl)-3-(6-(4-fluorophenyl)imidazo[2,1-b]thiazol-5-yl)prop-2-en-1-one; (11e)
(E)-1-(benzo[d][1,3]dioxol-5-yl)-3-(6-(trifluoromethyl)imidazo[2,1-b]thiazol-5-yl)prop-2-en-1-one; (11f)
(E)-1-(benzo[d][1,3]dioxol-5-yl)-3-(6-(4-methoxyphenyl)-2-methylimidazo[2,1-b]thiazol-5-yl)prop-2-en-1-one; (23a)
(E)-1-(benzo[d][1,3]dioxol-5-yl)-3-(6-(4-chlorophenyl)-2-methylimidazo[2,1-b]thiazol-5-yl)prop-2-en-1-one; (23b)
(E)-1-(benzo[d][1,3]dioxol-5-yl)-3-(6-(4-methoxy-3-nitrophenyl)-2-methylimidazo[2,1-b]thiazol-5-yl)prop-2-en-1-one; (23c)
(E)-1-(benzo[d][1,3]dioxol-5-yl)-3-(6-(4-chloro-3-nitrophenyl)-2-methylimidazo[2,1-b]thiazol-5-yl)prop-2-en-1-one; (23d)
(E)-1-(benzo[d][1,3]dioxol-5-yl)-3-(6-(4-fluorophenyl)-2-methylimidazo[2,1-b]thiazol-5-yl)prop-2-en-1-one; (23e)
(E)-1-(benzo[d][1,3]dioxol-5-yl)-3-(2-methyl-6-(trifluoromethyl)imidazo[2,1-b]thiazol-5-yl)prop-2-en-1-one; (23f)
(E)-3-(6-(4-methoxyphenyl)imidazo[2,1-b]thiazol-5-yl)-1-(naphthalen-2-yl) prop-2-en-1-one; (12a)
(E)-3-(6-(4-chlorophenyl)imidazo[2,1-b]thiazol-5-yl)-1-(naphthalen-2-yl) prop-2-en-1-one; (12b)
(E)-3-(6-(4-methoxy-3-nitrophenyl)imidazo[2,1-b]thiazol-5-yl)-1-(naphthalen-2-yl)prop-2-en-1-one; (12c)
(E)-3-(6-(4-chloro-3-nitrophenyl)imidazo[2,1-b]thiazol-5-yl)-1-(naphthalen-2-yl)prop-2-en-1-one; (12d)
(E)-3-(6-(4-fluorophenyl)imidazo[2,1-b]thiazol-5-yl)-1-(naphthalen-2-yl)prop-2-en-1-one; (12e)

(E)-1-(naphthalen-2-yl)-3-(6-(trifluoromethyl)imidazo[2,1-b]thiazol-5-yl)prop-2-en-1-one; (12f)

(E)-3-(6-(4-methoxyphenyl)-2-methylimidazo[2,1-b]thiazol-5-yl)-1-(naphthalen-2-yl) prop-2-en-1-one; (24a)

(E)-3-(6-(4-chlorophenyl)-2-methyl imidazo[2,1-b]thiazol-5-yl)-1-(naphthalen-2-yl)prop-2-en-1-one; (24b)

(E)-3-(6-(4-methoxy-3-nitrophenyl)-2-methylimidazo[2,1-b]thiazol-5-yl)-1-(naphthalen-2-yl)prop-2-en-1-one; (24c)

(E)-3-(6-(4-chloro-3-nitrophenyl)-2-methylimidazo[2,1-b]thiazol-5-yl)-1-(naphthalen-2-yl)prop-2-en-1-one; (24d)

(E)-3-(6-(4-fluorophenyl)-2-methylimidazo[2,1-b]thiazol-5-yl)-1-(naphthalen-2-yl)prop-2-en-1-one; (24e)

(E)-3-(2-methyl-6-(trifluoromethyl)imidazo[2,1-b]thiazol-5-yl)-1-(naphthalen-2-yl)prop-2-en-1-one; (24f)

(E)-1-(biphenyl-4-yl)-3-(6-(4-methoxyphenyl)imidazo[2,1-b]thiazol-5-yl)prop-2-en-1-one; (13a)

(E)-1-(biphenyl-4-yl)-3-(6-(4-chlorophenyl)imidazo[2,1-b]thiazol-5-yl)prop-2-en-1-one; (13b)

(E)-1-(biphenyl-4-yl)-3-(6-(4-methoxy-3-nitrophenyl)imidazo[2,1-b]thiazol-5-yl)prop-2-en-1-one; (13c)

(E)-1-(biphenyl-4-yl)-3-(6-(4-chloro-3-nitrophenyl)imidazo[2,1-b]thiazol-5-yl)prop-2-en-1-one; (13d)

(E)-1-(biphenyl-4-yl)-3-(6-(4-fluorophenyl)imidazo[2,1-b]thiazol-5-yl)prop-2-en-1-one; (13e)

(E)-1-(biphenyl-4-yl)-3-(6-(trifluoromethyl)imidazo[2,1-b]thiazol-5-yl)prop-2-en-1-one; (13f)

(E)-1-(biphenyl-4-yl)-3-(6-(4-methoxyphenyl)-2-methylimidazo[2,1-b]thiazol-5-yl)prop-2-en-1-one; (25a)

(E)-1-(biphenyl-4-yl)-3-(6-(4-chlorophenyl)-2-methylimidazo[2,1-b]thiazol-5-yl)prop-2-en-1-one; (25b)

(E)-1-(biphenyl-4-yl)-3-(6-(4-methoxy-3-nitrophenyl)-2-methylimidazo[2,1-b]thiazol-5-yl)prop-2-en-1-one; (25c)

(E)-1-(biphenyl-4-yl)-3-(6-(4-chloro-3-nitrophenyl)-2-methylimidazo[2,1-b]thiazol-5-yl)prop-2-en-1-one; (25d)

(E)-1-(biphenyl-4-yl)-3-(6-(4-fluorophenyl)-2-methylimidazo[2,1-b]thiazol-5-yl)prop-2-en-1-one; (25e)

(E)-1-(biphenyl-4-yl)-3-(2-methyl-6-(trifluoromethyl)imidazo[2,1-b]thiazol-5-yl)prop-2-en-1-one; (25f)

(E)-3-(6-(4-methoxyphenyl)imidazo[2,1-b]thiazol-5-yl)-1-(pyridin-4-yl)prop-2-en-1-one; (14a)

(E)-3-(6-(4-chlorophenyl)imidazo[2,1-b]thiazol-5-yl)-1-(pyridin-4-yl)prop-2-en-1-one; (14b)

(E)-3-(6-(4-methoxy-3-nitrophenyl)imidazo[2,1-b]thiazol-5-yl)-1-(pyridin-4-yl)prop-2-en-1-one; (14c)

(E)-3-(6-(4-chloro-3-nitrophenyl)imidazo[2,1-b]thiazol-5-yl)-1-(pyridin-4-yl)prop-2-en-1-one; (14d)

(E)-3-(6-(4-fluorophenyl)imidazo[2,1-b]thiazol-5-yl)-1-(pyridin-4-yl)prop-2-en-1-one; (14e)

(E)-1-(pyridin-4-yl)-3-(6-(trifluoromethyl)imidazo[2,1-b]thiazol-5-yl)prop-2-en-1-one; (14f)

(E)-3-(6-(4-methoxyphenyl)-2-methylimidazo[2,1-b]thiazol-5-yl)-1-(pyridin-4-yl)prop-2-en-1-one; (26a)

(E)-3-(6-(4-chlorophenyl)-2-methylimidazo[2,1-b]thiazol-5-yl)-1-(pyridin-4-yl)prop-2-en-1-one; (26b)

(E)-3-(6-(4-methoxy-3-nitrophenyl)-2-methyl imidazo[2,1-b]thiazol-5-yl)-1-(pyridin-4-yl)prop-2-en-1-one; (26c)

(E)-3-(6-(4-chloro-3-nitrophenyl)-2-methylimidazo[2,1-b]thiazol-5-yl)-1-(pyridin-4-yl)prop-2-en-1-one; (26d)

(E)-3-(6-(4-fluorophenyl)-2-methylimidazo[2,1-b]thiazol-5-yl)-1-(pyridin-4-yl)prop-2-en-1-one; (26e)

(E)-3-(2-methyl-6-(trifluoromethyl)imidazo[2,1-b]thiazol-5-yl)-1-(pyridin-4-yl)prop-2-en-1-one; (26f)

(E)-1-(1H-indol-3-yl)-3-(6-(4-methoxyphenyl)imidazo[2,1-b]thiazol-5-yl)prop-2-en-1-one; (15a)

(E)-3-(6-(4-chlorophenyl)imidazo[2,1-b]thiazol-5-yl)-1-(1H-indol-3-yl)prop-2-en-1-one; (15b)

(E)-1-(1H-indol-3-yl)-3-(6-(4-methoxy-3-nitrophenyl)imidazo[2,1-b]thiazol-5-yl)prop-2-en-1-one; (15c)

(E)-3-(6-(4-chloro-3-nitrophenyl)imidazo[2,1-b]thiazol-5-yl)-1-(1H-indol-3-yl)prop-2-en-1-one; (15d)

(E)-3-(6-(4-fluorophenyl)imidazo[2,1-b]thiazol-5-yl)-1-(1H-indol-3-yl)prop-2-en-1-one; (15e)

(E)-1-(1H-indol-3-yl)-3-(6-(trifluoromethyl)imidazo[2,1-b]thiazol-5-yl)prop-2-en-1-one; (15f)

(E)-1-(1H-indol-3-yl)-3-(6-(4-methoxyphenyl)-2-methylimidazo[2,1-b]thiazol-5-yl)prop-2-en-1-one; (27a)

(E)-3-(6-(4-chlorophenyl)-2-methylimidazo[2,1-b]thiazol-5-yl)-1-(1H-indol-3-yl)prop-2-en-1-one; (27b)

(E)-1-(1H-indol-3-yl)-3-(6-(4-methoxy-3-nitrophenyl)-2-methylimidazo[2,1-b]thiazol-5-yl)prop-2-en-1-one; (27c)

(E)-3-(6-(4-chloro-3-nitrophenyl)-2-methylimidazo[2,1-b]thiazol-5-yl)-1-(1H-indol-3-yl)prop-2-en-1-one; (27d)

(E)-3-(6-(4-fluorophenyl)-2-methylimidazo[2,1-b]thiazol-5-yl)-1-(1H-indol-3-yl)prop-2-en-1-one; (27e)

(E)-1-(1H-indol-3-yl)-3-(2-methyl-6-(trifluoromethyl)imidazo[2,1-b]thiazol-5-yl)prop-2-en-1-one; (27f)

(E)-3-(6-(4-methoxyphenyl)imidazo[2,1-b]thiazol-5-yl)-1-(thiophen-2-yl)prop-2-en-1-one; (16a)

(E)-3-(6-(4-chlorophenyl)imidazo[2,1-b]thiazol-5-yl)-1-(thiophen-2-yl)prop-2-en-1-one; (16b)

(E)-3-(6-(4-methoxy-3-nitrophenyl)imidazo[2,1-b]thiazol-5-yl)-1-(thiophen-2-yl)prop-2-en-1-one; (16c)

(E)-3-(6-(4-chloro-3-nitrophenyl)imidazo[2,1-b]thiazol-5-yl)-1-(thiophen-2-yl)prop-2-en-1-one; (16d)

(E)-3-(6-(4-fluorophenyl)imidazo[2,1-b]thiazol-5-yl)-1-(thiophen-2-yl)prop-2-en-1-one; (16e)

(E)-1-(thiophen-2-yl)-3-(6-(trifluoromethyl)imidazo[2,1-b]thiazol-5-yl)prop-2-en-1-one; (16f)

(E)-3-(6-(4-methoxyphenyl)-2-methylimidazo[2,1-b]thiazol-5-yl)-1-(thiophen-2-yl)prop-2-en-1-one; (28a)

(E)-3-(6-(4-chlorophenyl)-2-methylimidazo[2,1-b]thiazol-5-yl)-1-(thiophen-2-yl)prop-2-en-1-one; (28b)

(E)-3-(6-(4-methoxy-3-nitrophenyl)-2-methyl imidazo[2,1-b]thiazol-5-yl)-1-(thiophen-2-yl)prop-2-en-1-one; (28c)

(E)-3-(6-(4-chloro-3-nitrophenyl)-2-methylimidazo[2,1-b]thiazol-5-yl)-1-(thiophen-2-yl)prop-2-en-1-one; (28d)

(E)-3-(6-(4-fluorophenyl)-2-methylimidazo[2,1-b]thiazol-5-yl)-1-(thiophen-2-yl)prop-2-en-1-one; (28e)

(E)-3-(2-methyl-6-(trifluoromethyl)imidazo[2,1-b]thiazol-5-yl)-1-(thiophen-2-yl)prop-2-en-1-one; (28f)

(E)-3-(6-(4-methoxyphenyl)imidazo[2,1-b]thiazol-5-yl)-1-(1H-pyrrol-2-yl)prop-2-en-1-one; (17a)

(E)-3-(6-(4-chlorophenyl)imidazo[2,1-b]thiazol-5-yl)-1-(1H-pyrrol-2-yl)prop-2-en-1-one; (17b)

(E)-3-(6-(4-methoxy-3-nitrophenyl)imidazo[2,1-b]thiazol-5-yl)-1-(1H-pyrrol-2-yl)prop-2-en-1-one; (17c)

(E)-3-(6-(4-chloro-3-nitrophenyl)imidazo[2,1-b]thiazol-5-yl)-1-(1H-pyrrol-2-yl)prop-2-en-1-one; (17d)

(E)-3-(6-(4-fluorophenyl)imidazo[2,1-b]thiazol-5-yl)-1-(1H-pyrrol-2-yl)prop-2-en-1-one; (17e)

(E)-1-(1H-pyrrol-2-yl)-3-(6-(trifluoromethyl)imidazo[2,1-b]thiazol-5-yl)prop-2-en-1-one; (17f)

(E)-3-(6-(4-methoxyphenyl)-2-methylimidazo[2,1-b]thiazol-5-yl)-1-(1H-pyrrol-2-yl)prop-2-en-1-one; (29a)

(E)-3-(6-(4-chlorophenyl)-2-methylimidazo[2,1-b]thiazol-5-yl)-1-(1H-pyrrol-2-yl)prop-2-en-1-one; (29b)

(E)-3-(6-(4-methoxy-3-nitrophenyl)-2-methylimidazo[2,1-b]thiazol-5-yl)-1-(1H-pyrrol-2-yl)prop-2-en-1-one; (29c)

(E)-3-(6-(4-chloro-3-nitrophenyl)-2-methylimidazo[2,1-b]thiazol-5-yl)-1-(1H-pyrrol-2-yl)prop-2-en-1-one; (29d)

(E)-3-(6-(4-fluorophenyl)-2-methylimidazo[2,1-b]thiazol-5-yl)-1-(1H-pyrrol-2-yl)prop-2-en-1-one; (29e)

(E)-3-(2-methyl-6-(trifluoromethyl)imidazo[2,1-b]thiazol-5-yl)-1-(1H-pyrrol-2-yl)prop-2-en-1-one; (29f)
(E)-1-(furan-2-yl)-3-(6-(4-methoxyphenyl)imidazo[2,1-b]thiazol-5-yl)prop-2-en-1-one; (18a)
(E)-3-(6-(4-chlorophenyl)imidazo[2,1-b]thiazol-5-yl)-1-(furan-2-yl)prop-2-en-1-one; (18b)
(E)-1-(furan-2-yl)-3-(6-(4-methoxy-3-nitrophenyl)imidazo[2,1-b]thiazol-5-yl)prop-2-en-1-one; (18c)
(E)-3-(6-(4-chloro-3-nitrophenyl)imidazo[2,1-b]thiazol-5-yl)-1-(furan-2-yl)prop-2-en-1-one; (18d)
(E)-1-(furan-2-yl)-3-(6-(4-fluorophenyl)imidazo[2,1-b]thiazol-5-yl)prop-2-en-1-one; (18e)
(E)-1-(furan-2-yl)-3-(6-(trifluoromethyl)imidazo[2,1-b]thiazol-5-yl)prop-2-en-1-one; (18f)
(E)-1-(furan-2-yl)-3-(6-(4-methoxyphenyl)-2-methylimidazo[2,1-b]thiazol-5-yl)prop-2-en-1-one; (30a)
(E)-3-(6-(4-chlorophenyl)-2-methylimidazo[2,1-b]thiazol-5-yl)-1-(furan-2-yl)prop-2-en-1-one; (30b)
(E)-1-(furan-2-yl)-3-(6-(4-methoxy-3-nitrophenyl)-2-methylimidazo[2,1-b]thiazol-5-yl)prop-2-en-1-one; (30c)
(E)-3-(6-(4-chloro-3-nitrophenyl)-2-methylimidazo[2,1-b]thiazol-5-yl)-1-(furan-2-yl)prop-2-en-1-one; (30d)
(E)-3-(6-(4-fluorophenyl)-2-methylimidazo[2,1-b]thiazol-5-yl)-1-(furan-2-yl)prop-2-en-1-one; (30e)
(E)-1-(furan-2-yl)-3-(2-methyl-6-(trifluoromethyl)imidazo[2,1-b]thiazol-5-yl)prop-2-en-1-one. (30f)

In yet another embodiment of the present invention, Imidazothiazole-chalcone hybrids 7a, 7e, 7f, 8f and 19e exhibiting in vitro anticancer activity against human cancer cell lines selected from the group consisting of Leukemia cell lines (CCRF-CEM, MOLT-4, SR), CNS cell lines (SF-268, SF-539), Melanoma cell lines (LOX IMVI, M14, SK-MEL-5, UACC-257), Renal cell lines (A498, ACHN), lung cell lines (Hop-92), breast cell lines (MCF7, HS 578T), colon cell lines (COLO205), prostate cell lines (DU145, PC3) and ovarian cell lines (IGROV1, OVCAR-5).

In yet another embodiment, the concentration of the compounds 7a, 7e, 7f, 8f and 19e used for in vitro activity against leukemia cell lines for $GI_{50}$ is in the range of 1.66 to 3.08 μm, 1.55 to 2.23 μm, 0.54 to 1.92 μm, 0.49 to 2.33 μm, 1.55 to 2.23 μm and 0.80 to 7.19 μm respectively at an exposure period of at least 48 hrs.

In yet another embodiment, the concentration of the compounds 7a, 7e, 7f, 8f and 19e used for in vitro activity against lung cell lines for $GI_{50}$ is in the range of 0.24 to 3.70, 1.05 to 3.63, 1.65 to 7.00, 1.94 to 6.95 and 0.15 to 85.1 μm respectively at an exposure period of at least 48 hrs.

In yet another embodiment, the concentration of the compounds 7a, 7e, 7f, 8f and 19e used for in vitro activity against colon cell lines for GI50 is in the range of 1.77 to 3.45, 2.11 to 2.99, 1.01 to 1.94, 1.40 to 4.56 and 2.92 to 9.93 μm respectively at an exposure period of at least 48 hrs.

In yet another embodiment, the concentration of the compounds 7a, 7e, 7f, 8f and 19e used for in vitro activity against CNS cell lines for GI50 is in the range of 1.66 to 3.54 and 1.74 to 3.73, 1.38 to 2.67, 1.87 to 6.87 and 2.33 to 87.8 μm respectively at an exposure period of at least 48 hrs.

In yet another embodiment, the concentration of the compounds 7a, 7e, 7f, 8f and 19e used for in vitro activity against melanoma cell lines for GI50 is in the range of 1.30 to 5.42, 1.82 to 8.27, 1.36 to 2.26, 0.60 to 8.48 and 0.51 to 7.07 μm respectively at an exposure period of at least 48 hrs.

In yet another embodiment, the concentration of the compounds 7a, 7e, 7f, 8f and 19e used for in vitro activity against ovarian cell lines for GI50 is in the range of 0.21 to 4.05, 1.04 to 3.78, 1.86 to 3.08, 1.88 to 4.18, 2.28 to >100 μm respectively at an exposure period of at least 48 hrs.

In yet another embodiment, the concentration of the compounds 7a, 7e, 7f, 8f and 19e used for in vitro activity against renal cell lines for GI50 is in the range of 1.12 to 5.04, 0.04 to 5.81, 1.56 to 2.30, 2.46 to 8.76 and 1.78 to 28.0 μM respectively, at an exposure period of at least 48 hrs.

In yet another embodiment, the concentration of the compounds 7a, 7e, 7f, 8f and 19e used for in vitro activity against prostate cell lines for GI50 is in the range of 2.62 to 3.10, 2.45 to 3.43, 1.41 to 2.66, 1.64 to 5.39 and 2.41 to 7.52 μm respectively at an exposure period of at least 48 hrs.

In yet another embodiment, the concentration of the compounds 7a, 7e, 7f, 8f and 19e used for in vitro activity against breast cell lines for IC50 is in the range of 1.90 to 3.46, 2.05 to 3.76, 1.25 to 2.92, 0.76 to 6.18 and 1.81 to 8.29 μm respectively at an exposure period of at least 48 hrs.

In yet another embodiment of the present invention, the invention provides a process for preparation of novel imidazothiazole-chalcone hybrids of general formula, A which includes structures from 7a-f to 18a-f and 19a-f to 30a-f, comprising the steps of:
i. providing imidazothiazole aldehyde of formula 5;

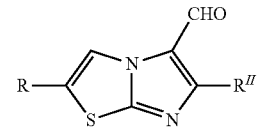

ii. reacting the imidazothiazole aldehyde of formula 5 with the substituted ketone of formula 6 wherein R' represent trimethoxyphenyl, dimethoxyphenyl, dimethylphenyl, difluorophenyl, benzo[d][1,3]dioxolylnaphthalenyl, biphenyl, pyridinyl, indolyl, thiophenyl, pyrrolyl and furanyl in ethanol in the presence of 10-15% aqueous solution selected from the group consisting of sodium hydroxide, potassium hydroxide or barium hydroxide;

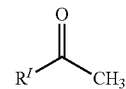

iii. evaporating the organic solvent to obtain the residue which was dissolved in ethylacetate/water;
iv. washing the organic layer with brine and evaporated;
v. purifying by column chromatography to obtain the desired products of formulae 7a-f to 18a-f and 19a-f to 30a-f wherein R represent hydrogen and methyl, R' represent trimethoxyphenyl, dimethoxyphenyl, dimethylphenyl, difluorophenyl, benzo[d][1,3]dioxolylnaphthalenyl, biphenyl, pyridinyl, indolyl, thiophenyl, pyrrolyl and furanyl and R"represent methoxyphenyl, chlorophenyl, methoxynitrophenyl, chloronitrophenyl, fluorophenyl and trifluoromethyl.

DETAILED DESCRIPTION OF THE INVENTION

The precursor imidazothiazole aldehyde of formula 5, has been prepared by using starting compounds 1 and 2 using literature methods "Aldo Andreani, Silvia Burnelli, Massimiliano Granaiola, Alberto Leoni, Alessandra Locatelli *J. Med. Chem.* 2008, 51, 809-816, Aldo Andreani, Silvia Burnelli, Massimiliano Granaiola, Alberto Leoni, Alessandra Locatelli, *J. Med. Chem.* 2007, 50, 3167-3172, Aldo Andreani, Massimiliano Granaiola, Alberto Leoni, Alessandra Locatelli, Rita Morigi, Mirella Rambaldi, Giorgio Lenaz, Romana Fato, Christian Bergamini, and Giovanna Farruggia *J. Med. Chem.*, 2005, 48, 3085-3089 and Aldo Andreani, Silvia Burnelli, Massimiliano Granaiola, Alberto Leoni, Alessandra Locatelli, Rita Morigi, Mirella Rambaldi, Lucilla Varoli, Natalia Calonghi, Concettina Cappadone, Giovanna Farruggia, Maddalena Zini, Claudio Stefanelli, Lanfranco Masotti, Norman S. Radin and Robert H. Shoemaker, *J. Med. Chem.* 2005, 48, 3085-3089."

Figure 1:
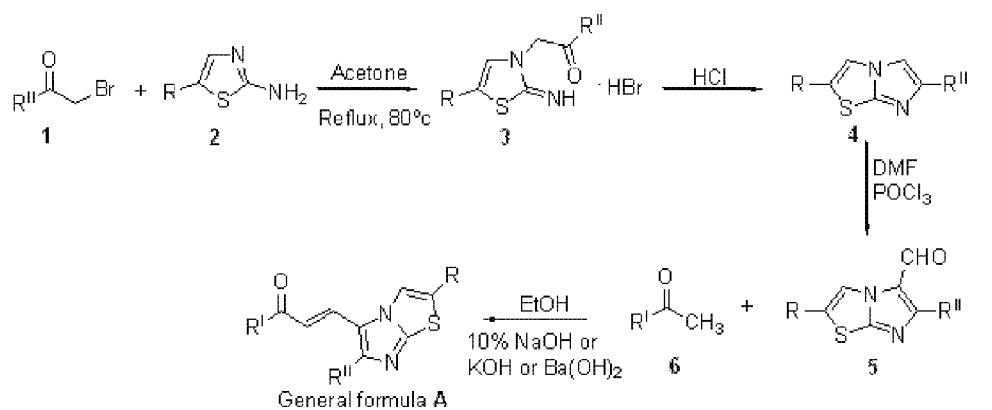
FIG. 1 shows a process of preparation of imidazothiazole-chalcone hybrids of formula A.
Figure 1:
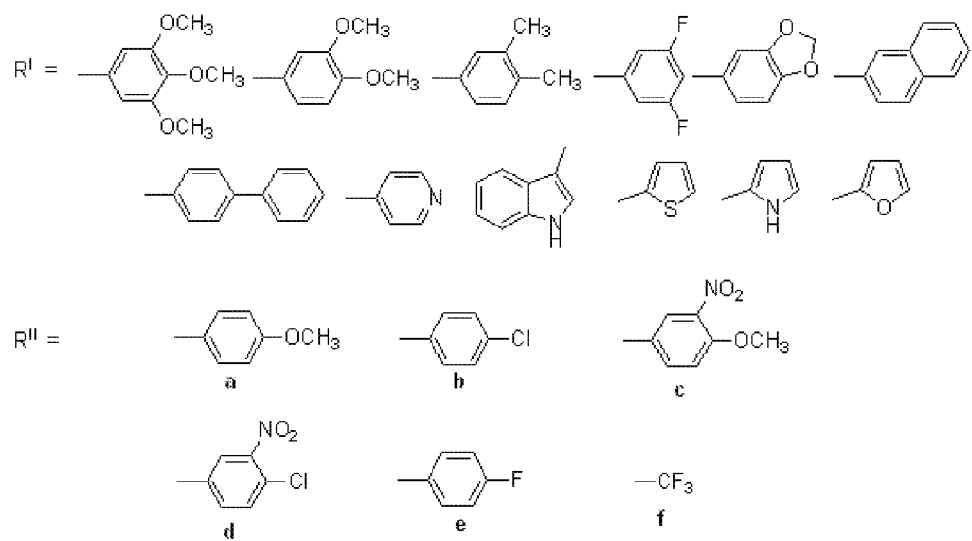
Figure 2:
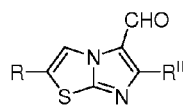
FIG. 2 shows a structure of formula 5.
Figure 2:
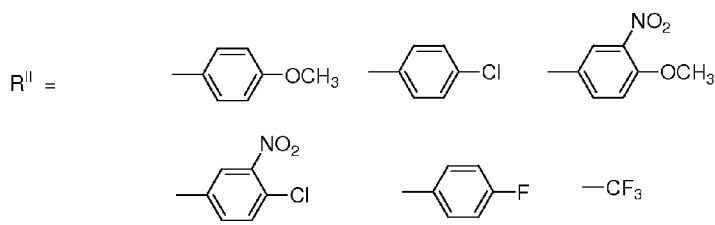
Figure 3:
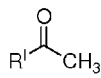
FIG. 3 shows a structure of formula 6.
Figure 3:
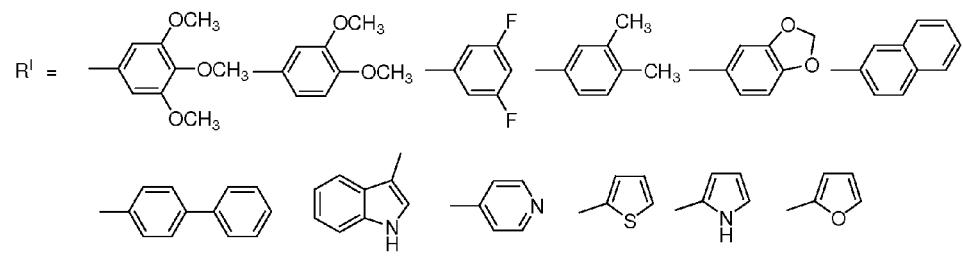

These new analogues of imidazothiazole-chalcone hybrids have shown promising anticancer activity in various cell lines. The molecules synthesized are of immense biological significance. This resulted in design and synthesis of new congeners as illustrated in FIG. 1 which comprise:
1. Formation of chalcone by reaction of imidazothiazole aldehyde of formula 5 (also see FIG. 2) with acetophenones of formula 6 (also see FIG. 3).
2. Stirring the reaction mixtures at room temperature 25-35° C. for 4 h in ethanol in the presence of 10% aqueous solution of NaOH.
3. Purification by column chromatography using different solvents like ethylacetate, hexane, dichloromethane and methanol.

EXAMPLES

The present invention will be more specifically explained by following examples. However, the scope of the present invention is not limited to the scope of these examples below.

Example 1

(E)-3-(6-(4-methoxyphenyl)imidazo[2,1-b]thiazol-5-yl)-1-(3,4,5-trimethoxyphenyl) prop-2-en-1-one (7a)

To a stirred solution of trimethoxy acetophenone (210 mg, 1.0 mmol) and a 6-(4-methoxyphenyl)imidazo[2,1-b]thiazol-5-carbaldehyde (258 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (7a) as yellow solid (360 mg, 80% yield). Mp: 177-179° C.

$^1$H NMR (CDCl3, 200 MHz) δ 3.86 (s, 3H), 3.92 (s, 9H), 6.96-7.06 (m, 3H), 7.18 (s, 2H), 7.19 (d, 1H, J=15.51 .Hz), 7.66 (d, 1H, J=8.53 .Hz), 7.82 (d, 1H, J=3.87 .Hz), 8.04 (d, 1H, J=15.51 .Hz), ESI-MS: 451.51 (M+H)$^+$.

Example 2

(E)-3-(6-(4-fluorophenyl)imidazo[2,1-b]thiazol-5-yl)-1-(3,4,5-trimethoxyphenyl)prop-2-en-1-one (7e)

To a stirred solution of trimethoxy acetophenone (210 mg, 1.0 mmol) and a 6-(4-fluorophenyl)imidazo[2, 1-1)]thiazol-5-carbaldehyde (246 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (7e) as yellow solid (328 mg, 75% yield). Mp: 222-225° C.

$^1$H NMR (CDCl3, 400 MHz) δ 3.89-3.92 (br, 9H) 7.05 (d, 1H J=4.39 Hz), 7.13 (s, 2H), 7.15 (d, 1H, J=15.38 .Hz), 7.17 (d, 1H, J=8.05 Hz), 7.24 (d, 1H, J=8.05 Hz), 7.70 (dd, 2H, J=5.12 Hz), 7.83 (d, 1H, J=4.39 Hz), 7.96 (d, 1H, J=15.38 Hz), ESI-MS: 439.47 (M+H)$_4$.

Example 3

(E)-3-(6-(trifluoromethyl)imidazo[2,1-b]thiazol-5-yl)-1-(3,4,5-trimethoxyphenyl)prop-2-en-1-one (7f)

To a stirred solution of trimethoxy acetophenone (210 mg, 1.0 mmol) and a 6-(trifluoromethyl)imidazo[2,1-b]thiazole-5-carbaldehyde (220 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (70 as yellow solid (329 mg, 80% yield). Mp: 177-180° C.

$^1$H NMR (CDCl3, 300 MHz) δ 3.94-3.96 (b, 9H), 7.17 (d, 1H, J=15.86 Hz), 7.21-7.22 (b, 2H), 7.33 (d, 1H, J=5.86 Hz), 7.83 (d, 1H, J=4.53 Hz), 7.90 (d, 1H J=15.86 Hz), ESI-MS: 413.38 (M+H)$^+$.

Example 4

(E)-1-(3,4-dimethoxyphenyl)-3-(6-(4-fluorophenyl) imidazo[2,1-b]thiazol-5-yl)prop-2-en-1-one (8e)

To a stirred solution 3,4-dimethoxyphenyl acetophenone (180 mg, 2.7 mmol) and a 6-(4-fluorophenyl)imidazo[2,1-b] thiazol-5-carbaldehyde (246 mg, 2.7 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by columnchromatography using ethyl acetate:hexane (2:8) as a solvent system to obtain the pure product (8e) as yellow solid (306 mg, 75% yield). Mp: 221-223° C.

$^1$H NMR (CDCl3, 300 MHz) δ 3.96 (s, 6H), 6.90 (d, 1H, J=8.30 Hz), 7.07 (d, 1H, J=4.53 .Hz), 7.15-7.22 (m, 2H), 7.29 (d, 1H, J=15.86 Hz), 7.53-7.59 (m, 2H), 7.69-7.75 (m, 2H) 7.86 (d, 1H, J=4.53 Hz), 8.02 (d, 1H J=15.86 Hz), ESI-MS: 409.45 (M+H)$^+$.

Example 5

(E)-1-(3,4-dimethoxyphenyl)-3-(6-(trifluoromethyl) imidazo[2,1-b)]thiazol-5-yl) Prop-2-en-1-one (8f)

To a stirred solution 3,4-dimethoxyphenyl acetophenone (180 mg, 2.7 mmol) and a 6-(trifluoromethyl)imidazo[2,1-b]

thiazole-5-carbaldehyde (246 mg, 2.7 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by columnchromatography using ethyl acetate:hexane (2:8) as a solvent system to obtain the pure product (80 as yellow solid (306 mg, 75% yield). Mp: 167-169° C.

$^1$H NMR (CDCl3, 300 MHz) δ 3.97 (s, 6H), 6.93 (d, 1H, J=9.065 Hz), 7.19 (d, 1H, J=4.53 Hz), 7.41 (d, 1H, J=15.86 Hz), 7.57-7.61 (m, 2H), 7.83 (d, 1H, J=4.53 Hz), 7.91 (d, 1H J=15.86 Hz), ESI-MS: 382.35 (M+H)$^+$.

Example 6

(E)-1(3,5-difluorophenyl)-3-(6-(4-methoxyphenyl) imidazo[2,1-b]thiazo-5-yl)prop-2-en-1-one (10a)

To a stirred solution of 3,5 difluoro phenyl acetophenone (156 mg, 1.0 mmol) and a 6-(4-methoxyphenyl)imidazo[2,1-b]thiazol-5-carbaldehyde (258 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (10a) as yellow solid (364 mg, 92% yield). Mp: 234-236° C.

$^1$H NMR (CDCl3, 300 MHz) δ 3.87 (s, 3H), 7.0-7.08 (m, 3H), 7.02 (d, 1H, J=3.77 Hz), 7.07 (d, 1H J=15.86 Hz), 7.43-7.48 (m, 2H,) 7.65 (d, 2H, J=4.83 Hz), 7.87 (d, 1H, J=4.53 Hz), 8.09 (d, 1H, J=15.10 Hz), ESI-MS: 397.46 (M+H)$^+$.

Example 7

(E)-1-(benzo[d][1,3]dioxol-5-yl)-3-(6-(4-methoxyphenyl)imidazo[2,1-b]thiazol-5-yl)prop-2-en-1-one (11a)

To a stirred solution 3,4-methylenedioxy phenyl acetophenone (164 mg, 1.0 mmol) and a 6-(4-methoxyphenyl)imidazo[2,1-b]thiazol-5-carbaldehyde (258 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (11a) as yellow solid (323 mg, 80% yield). Mp: 189-191° C.

$^1$H NMR (CDCl3, 200 MHz) ; δ 3.86 (s, 3H), 6.083 (s, 2H), 6.86 (d, 1H, J=8.08 Hz), 6.95-7.04 (m, 3H), 7.17 (d, 1H, J=15.42 Hz), 7.54-7.68 (m, 4H,) 7.84 (d, 1H, J=4.40 Hz), 8.03 (d, 1H, J=15.42 Hz), ESI-MS: 405.44 (M+H)$^+$.

Example 8

(E)-1-(3,4-dimethylphenyl)-3-(6-(4-fluorophenyl) imidazo[2,1-b]thiazol-5-yl)prop-2-en-1-one (9e)

To a stirred solution of 3,4-dimethylphenyl acetophenone (148 mg, 1.0 mmol) and a 6-(4-fluorophenyl)imidazo[2,1-b]thiazol-5-carbaldehyde (246 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (9e) as yellow solid (286 mg, 76% yield). Mp: 210-213° C.

$^1$H NMR (CDCl3, 300 MHz) δ 2.34-2.36 (b, 6H), 7.06 (dd, 2H, J=4.53 Hz), 7.14-7.19 (m, 2H), 7.23 (d, 1H J=15.10 Hz), 7.22-7.27 (m, 3H), 7.65-7.74 (m,4H), 7.87 (d,1H,J=4.53 Hz) 7.99 (d,1H,J=15.10 Hz), ESI-MS: 377.45 (M+H)$^+$.

Example 9

(E)-3-(6-(4-fluorophenyl)imidazo[2,1-b]thiazol-5-yl)-1-(naphthalen-2-yl)prop-2-en-1-one (12e)

To a stirred solution of 2-acetyl napthalene (170 mg, 1.0 mmol) and a 6-(4-fluorophenyl) imidazo[2,1-b]thiazol-5-carbaldehyde (246 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (12e) as yellow solid (298 mg, 75% yield). Mp: 216-218° C.

$^1$H NMR (CDCl3, 400 MHz) δ 6.34 (t, 2H, J=8.95 Hz), 6.62 (d, 1H J=15.22 Hz), 6.62 (d, 1H, J=4.47 Hz), 6.65-6.75 (m, 3H), 6.86-6.89 (d, 1H J=15.22 Hz), 6.96-7.02 (m, 2H), 7.08-7.15 (m, 2H), 7.71 (d, 1H J=4.47 Hz),7.87-7.89 (b,1H), ESI-MS: 399.45 (M+H)$^+$.

Example 10

(E)-1-(biphenyl-4-yl)-3-(6-(4-fluorophenyl)imidazo [2, 1-1)]thiazol-5-yl)prop-2-en-1-one (13e)

To a stirred solution of biphenyl acetophenone (196 mg, 1.0 mmol) and a 6-(4-fluorophenyl)imidazo[2,1-1)]thiazol-5-carbaldehyde (246 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (13e) as yellow solid (360 mg, 85% yield). Mp: 194-196° C.

$^1$H NMR (CDCl3, 300 MHz) δ 7.10 (d, 1H, J=4.53 Hz), 7.16-7.22 (m, 2H), 7.31 (d, 1H, J=15.86 Hz), 7.38-7.51 (m,

4H), 7.63-7.65 (m, 1H), 7.70-7.75 (m, 4H), 7.91 (d, 1H, J=4.53 Hz), 8.03-8.07 (m, 2H), 8.08 (d,1H, J=15.86 Hz), ESI-MS: 425.49 (M+H)$^+$.

Example 11

(E)-3-(6-(4-methoxyphenyl)imidazo[2,1-b]thiazol-5-yl)-1-(thiophen-2-yl)prop-2-en-1-one (16a)

To a stirred solution of 2-acetyl thiophene (126 mg, 1.0 mmol) and a 6-(4-methoxyphenyl) imidazo[2,1-b]thiazol-5-carbaldehyde (258 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (16a) as yellow solid (256 mg, 70% yield). Mp: 169-172° C.

$^1$H NMR (CDCl3, 300 MHz) } δ 3.86 (s, 3H), 7.01 (d, 1H J=15.86 Hz), 7.0-7.02 (bs, 2H), 7.13-7.17 (m, 2H),7.62-7.67 (m, 3H) 7.77 (d, 1H, J=3.02 Hz),7.84 (d, 1H, J=4.53 Hz), 8.05 (d, 1H, J=15.86 Hz), ESI-MS: 367.46 (M+H)$^+$.

Example 12

(E)-3-(6-(4-methoxyphenyl)imidazo[2,1-b]thiazol-5-yl)-1-(1H-pyrrol-2-yl)prop-2-en-1-one (17a)

To a stirred solution of 2-acetyl pyrrole (109 mg, 1.0 mmol) and a 6-(4-methoxyphenyl) imidazo[2,1-b]thiazol-5-carbaldehyde (258 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (17a) as yellow solid (286 mg, 82% yield). Mp: 177-179° C.

$^1$H NMR (CDCl3, 300 MHz) } δ 3.88 (s, 3H), 6.23-6.27 (m, 1H), 7.0-7.09 (m, 3H), 7.30 (d, 1H, J=16.09 Hz), 7.35-7.37 (m, 2H), 7.63 (d, 2H J=8.77 Hz), 7.90 (d,1H, J=16.09 Hz),8.45 (d,1H J=4.38 Hz), ESI-MS: 350.41 (M+H)$^+$.

Example 13

(E)-3-(6-(4-fluorophenyl)-2-methylimidazo[2,1-b]thiazol-5-yl)-1-(3,4,5-trimethoxy-phenyl)trimethoxyphenyl)prop-2-en-1-one (19e)

To a stirred solution of trimethoxy acetophenone (210 mg, 1.0 mmol) and a 6-(4-fluorophenyl)imidazo[2,1-b]thiazol-5-carbaldehyde (260 mg, 1.0 mmol) in ethanol (20 ml) 10% aqueous solution of NaOH was added (5 ml). The reaction mixture was stirred at room temperature 27° C. for 4 h and the reaction was monitored by TLC using ethyl acetate-hexane (3:7) as a solvent system. The solvent was evaporated under vacuum then the residue was dissolved in ethylacetate/water. The organic layer was washed with brine and evaporated. This was further purified by column chromatography using ethyl acetate:hexane (2:8) as a solvent system to obtain the pure product (19e) as yellow solid (362 mg, 80% yield). Mp: 159-162° C.

$^1$H NMR (CDCl3, 400 MHz) } δ 2.54 (s, 3H), 3.79 (s, 3H), 3.90 (s, 6H), 7.33 (s, 2H), 7.49 (d, 1H J=15.53 Hz), 7.67 (dd, 2H J=5.18 Hz), 7.82 (d, 1H J=15.53 Hz), 8.22 (s, 2H), 8.40 (s, 1H), ESI-MS: 453.56 (M+H)$^+$.

BIOLOGICAL ACTIVITY

Some of in vitro biological activity studies were carried out at the National Cancer Institute, Maryland, USA.

In Vitro Cytotoxicity

The imidazothiazole-chalcone hybrids 7a, 7e, 7f, 8f and 19e have been tested against sixty human tumour cell lines derived from nine cancer types (leukemia, non-small cell lung cancer, colon cancer, CNS cancer, melanoma, ovarian cancer, renal cancer, prostate cancer and breast cancer) as per NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. The concentration for 50% cell growth inhibition ($GI_{50}$), total cell growth inhibition (TGI, 0% growth) and 50% cell death ($LC_{50}$, 50% growth) compared with the control has been calculated (Table-1). Compounds 7a, 7e, 7f, 8f and 19e have been evaluated for their in vitro cytotoxicity in sixty cell lines from nine human cancer types of lung (A549/ATCC, Hop-92, NCI-H226), leukemia cell lines (K-562, HL-60 (TB), colon cell lines (HCT-116, COLO 205, HCC-2998), CNS cell lines (SF-539), melanoma cell lines (SK-MEL-5, UACC-62, M14), ovarian cell lines (IGROV1), renal cell lines (CAKI-1), prostate cell lines (DU-145) and breast cell lines (BT-549, MDA-MB-435, HS578T) origin. The results are expressed as percent of cell growth determined relative to that of untreated control cells (Table 2). The representative compounds 7a, 7e, 7f, 8f and 19e have shown significant cytotoxicity against some cancer cell lines.

TABLE 1

$Log_{10}$ $GI_{50}$ (concentration in mol/L causing 50% growth inhibition) values for imidazothiazole-chalcone hybrids (7a, 7e, 7f, 8f and 19e)

| | Leukemia | Non-small-celllung | Colon | CNS | Melanoma | Ovarian | Renal | Prostate | Breast |
|---|---|---|---|---|---|---|---|---|---|
| $Log_{10}$ GI50 7a | −5.65 | −5.71 | −5.58 | −5.58 | −5.58 | −5.73 | −5.60 | −5.54 | −5.60 |
| $Log_{10}$ LC50 7a | −4.00 | −4.02 | −4.14 | −4.00 | −4.15 | −4.15 | −4.00 | −4.00 | −4.00 |

TABLE 1-continued

Log$_{10}$ GI$_{50}$ (concentration in mol/L causing 50% growth inhibition) values for imidazothiazole-chalcone hybrids (7a, 7e, 7f, 8f and 19e)

| | Leukemia | Non-small-celllung | Colon | CNS | Melanoma | Ovarian | Renal | Prostate | Breast |
|---|---|---|---|---|---|---|---|---|---|
| Log$_{10}$ GI50 7e | −5.73 | −5.65 | −5.58 | −5.63 | −5.58 | −5.66 | −5.81 | −5.53 | −5.55 |
| Log$_{10}$ LC50 7e | −4.15 | −4.25 | −4.42 | −4.28 | −4.37 | −4.28 | −4.06 | −4.00 | −4.00 |
| Log$_{10}$ GI50 7f | −5.89 | −5.61 | −5.79 | −5.72 | −5.77 | −5.57 | −5.73 | −5.71 | −5.68 |
| Log$_{10}$ LC50 7f | −4.00 | −4.57 | −5.07 | −4.90 | −5.03 | −4.24 | −4.98 | −4.70 | −4.61 |
| Log$_{10}$ GI50 8f | −5.83 | −5.40 | −5.61 | −5.47 | −5.44 | −5.53 | −5.31 | −5.53 | −5.53 |
| Log$_{10}$ LC50 8f | −4.00 | −4.00 | −4.00 | −4.00 | −4.00 | −4.00 | −4.00 | −4.00 | −4.00 |
| Log$_{10}$ GI50 19e | −5.57 | −5.35 | −5.30 | −4.90 | −5.52 | −5.17 | −5.20 | −5.37 | −5.44 |
| Log$_{10}$ LC50 19e | −4.00 | −4.00 | −4.00 | −4.00 | −4.00 | −4.00 | −4.00 | −4.00 | −4.00 |

Each cancer type represents the average of six to eight different cancer cell lines.

The compounds 7a, 7e, 7f, 8f and 19e exhibit a wide spectrum of activity against sixty cell lines in nine cell panels, with GI$_{50}$ value of <9 μm. In the Leukemia cancer panel, the growths of SR cell lines were affected by compounds 7f, 8f and 19f with GI$_{50}$ values as 0.54, 0.49 and 0.80 μM respectively. In the non-small cell lung cancer panel, the growth of HOP-92 cell line was affected by compounds 7a, 7e and 19e with GI$_{50}$ values as 0.24, 1.05 and 0.15 μM respectively. The GI$_{50}$ values of compounds 7a and 7f against colon cancer HCC-2998, HCT-116 cell lines are 1.77, 1.88 and 1.71, 1.01 μM respectively. The GI$_{50}$ values for compounds 7a and 19e against melanoma SK-MEL-5 cell line are 1.30 and 0.51 μm respectively. The GI$_{50}$ value for compound 8f against melanoma LOX IMVI cell line is 0.60 μm. The GI$_{50}$ values for compounds 7a and 7e against ovarian cancer IGROV1 cell line are 0.21 and 1.04 μM respectively, and The GI$_{50}$ values for compound 7a against ovarian cancer OVCAR-5, OVCAR-8 cell lines are 1.99, 2.01 μM respectively. The GI$_{50}$ values for compounds 7a and 7e against renal CAKI-1 cell line are 1.20 and 0.04 μm respectively. The GI$_{50}$ values for compounds 7f and 8f against prostate cancer DU-145 cell line are 1.41 and 1.64 μm respectively. The GI$_{50}$ values for compounds 7f, 8f and 19e against breast cancer MCF7 cell line are 1.25, 0.76 and 1.81 μm respectively.

Compounds 7a, 7e, 7f, 8f and 19e exhibits activity against sixty cell lines in nine cancer cell panels with GI$_{50}$ values of <9 μm. in vitro cytotoxicity of compounds 7a, 7e, 7f, 8f and 19e in selected cancer cell lines has been illustrated in Table 2. The average GI$_{50}$ values for each cancer panel of compounds 7a, 7e, 7f, 8f and 19e have been illustrated in Table2.

TABLE 2

In vitro cytotoxicity of compounds 7a, 7e, 7f, 8f and 19e in sixty cancer cell lines

| Cancer panel/cell line | GI$_{50}$(μm)7a | GI$_{50}$(μm)7e | GI$_{50}$(μm)7f | GI$_{50}$(μm)8f | GI$_{50}$(μm)19e |
|---|---|---|---|---|---|
| Leukemia | | | | | |
| CCRF-CEM | 3.08 | 2.23 | 1.24 | 2.33 | 7.19 |
| HL-60(TB) | 1.66 | 1.77 | 1.83 | 1.00 | 2.8 |
| K-562 | 1.72 | 1.55 | 1.74 | 2.25 | 5.46 |
| MOLT-4 | 2.52 | 2.07 | 1.92 | 2.22 | 1.62 |
| SR | 2.33 | 1.73 | 0.54 | 0.49 | 0.80 |
| RPMI-8226 | — | — | 1.08 | 1.62 | 2.32 |
| Non-small cell lung | | | | | |
| A549/ATCC | 2.21 | 2.09 | 3.44 | 4.65 | 9.34 |
| EKVX | 3.12 | 2.74 | 2.72 | 4.43 | 2.29 |
| HOP-62 | 2.21 | 2.25 | 1.93 | 6.00 | 85.1 |
| HOP-92 | 0.24 | 1.05 | 7.00 | 5.8 | 0.15 |
| NCI-H226 | 2.58 | 1.89 | 2.17 | 6.95 | 9.58 |

TABLE 2-continued

In vitro cytotoxicity of compounds 7a, 7e, 7f, 8f and 19e in sixty cancer cell lines

| Cancer panel/cell line | GI$_{50}$(μm)7a | GI$_{50}$(μm)7e | GI$_{50}$(μm)7f | GI$_{50}$(μm)8f | GI$_{50}$(μm)19e |
|---|---|---|---|---|---|
| NCI-H23 | 2.18 | 2.49 | 1.72 | 2.78 | 2.24 |
| NCI-H322M | 3.70 | 3.63 | 1.96 | 3.17 | 8.65 |
| NCI-H460 | 2.70 | 2.30 | 1.65 | 1.94 | 3.87 |
| NCI-H522 | 1.97 | 2.32 | 2.03 | 2.91 | 2.96 |
| Colon | | | | | |
| COLO 205 | 2.52 | 2.79 | 1.94 | 4.56 | 4.94 |
| HCC-2998 | 1.77 | 2.11 | 1.71 | 5.07 | 9.93 |
| HCT-116 | 1.88 | 2.33 | 1.01 | 1.40 | 2.92 |
| HCT-15 | 3.45 | 2.94 | 1.80 | 2.54 | 3.76 |
| HT29 | 3.12 | 2.84 | 1.83 | 2.01 | 6.96 |
| KM12 | 2.65 | 2.30 | 1.47 | 1.97 | 3.63 |
| SW-620 | 3.16 | 2.99 | 1.67 | 1.49 | 5.34 |
| CNS | | | | | |
| SF-268 | 2.89 | 2.52 | 1.74 | 3.44 | 15.2 |
| SF-295 | 2.73 | 1.80 | 2.58 | 3.14 | 2.33 |
| SF-539 | 1.66 | 1.74 | 1.55 | 2.36 | 6.23 |
| SNB-19 | 3.54 | 3.73 | 2.67 | 4.25 | 87.8 |
| SNB-75 | 2.29 | 2.46 | 1.87 | 6.87 | 50.1 |
| U251 | 3.05 | 2.18 | 1.38 | 1.87 | 4.07 |
| Ovarian | | | | | |
| IGROV1 | 0.21 | 1.04 | 2.66 | 3.15 | 8.71 |
| OVCAR-3 | 2.23 | 2.16 | 1.86 | 2.12 | 3.66 |
| OVCAR-4 | 4.05 | 3.78 | 3.05 | 4.08 | 2.28 |
| OVCAR-5 | 1.99 | 1.92 | — | 4.18 | >100 |
| OVCAR-8 | 2.01 | 1.98 | 3.08 | 2.40 | 4.94 |
| NCI/ADR-RES | 2.57 | 2.10 | — | 1.88 | 2.63 |
| SK-OV-3 | 3.28 | 3.02 | 2.87 | 3.41 | 6.12 |
| Renal | | | | | |
| 786-0 | 2.58 | 2.51 | 1.76 | 5.67 | 8.88 |
| A498 | 2.99 | 2.73 | 1.89 | 7.58 | — |
| ACHN | 4.08 | 2.96 | 1.82 | 5.10 | 5.83 |
| CAKI-1 | 1.20 | 0.04 | 1.76 | 2.46 | 1.78 |
| RXF 393 | — | — | 2.02 | 2.51 | 5.75 |
| SN12C | 2.88 | 1.88 | 1.56 | 2.98 | 9.01 |
| TK-10 | 5.04 | 5.81 | 2.30 | 8.76 | 28.0 |
| UO-31 | 1.12 | 2.03 | 1.87 | 8.47 | 2.95 |
| Prostate | | | | | |
| PC-3 | 3.10 | 3.43 | 2.66 | 5.39 | 2.41 |
| DU-145 | 2.62 | 2.45 | 1.41 | 1.64 | 7.52 |
| Breast | | | | | |
| MCF7 | 2.02 | 2.24 | 1.25 | 0.76 | 1.81 |
| MDA-MB-231/ATCC | 2.55 | 2.49 | 2.92 | 5.91 | 5.38 |
| HS 578T | 1.90 | 2.05 | — | 2.51 | 8.29 |
| BT-549 | 3.46 | 3.76 | 2.26 | 3.25 | 3.75 |
| T-47D | 2.26 | 3.25 | 2.12 | 2.90 | 2.93 |
| MDA-MB-468 | 2.96 | 3.17 | — | 6.18 | 2.38 |
| Melanoma | | | | | |
| LOX IMVI | 2.42 | 1.85 | 1.36 | 0.60 | 2.50 |
| MALME-3M | 5.42 | 8.27 | 1.59 | 5.92 | 2.69 |
| M14 | 2.33 | 2.75 | — | 2.67 | 5.12 |
| MDAMB-435 | 2.85 | 1.82 | 1.61 | 1.85 | 1.75 |
| SK-MEL-2 | 2.42 | 2.52 | 2.26 | 4.08 | 5.75 |
| SK-MEL-28 | 4.11 | 4.19 | 1.69 | 8.48 | 7.07 |
| SK-MEL-5 | 1.30 | 1.45 | 1.59 | 4.20 | 0.51 |
| UACC-62 | 2.08 | 1.82 | 1.52 | 4.85 | 2.91 |
| UACC-25 | — | — | 1.90 | 7.77 | 4.75 |

The mean graph mid point values of $\log_{10}$ TGI and $\log_{10}$ LC$_{50}$ as well as $\log_{10}$ GI$_{50}$ for 7a, 7e, 7f, 8f and 19e are listed in Table-3. As demonstrated by mean graph pattern, compounds 7a, 7e, 7f, 8f and 19e exhibit an interesting profile of activity and selectivity for various cell lines. The mean graph mid points of $\log_{10}$ TGI and $\log_{10}$ LC$_{50}$ have shown similar pattern to the $\log_{10}$ GI$_{50}$ mean graph mid points.

TABLE 3

$\log_{10}$ GI$_{50}$, $\log_{10}$ TGI and $\log_{10}$ LC$_{50}$ mean graphs midpoints (MG_MID) of in vitro cytotoxicity data for the compounds 7a, 7e, 7f, 8f and 19e.against human tumour cell lines.

| Compound | Log$_{10}$ GI$_{50}$ | Log$_{10}$ TGI | Log$_{10}$ LC$_{50}$ |
| --- | --- | --- | --- |
| 7a | −5.63 | −4.76 | −4.06 |
| 7e | −5.65 | −5.02 | −4.23 |
| 7f | −5.72 | −5.28 | −4.72 |
| 8f | −5.51 | −4.22 | −4.00 |
| 19e | −5.32 | −4.14 | −4.02 |

TABLE 4

Comparative efficacy of Imidazothiazole-Chalcone derivatives of the present invention with Kown Chalcones & Imidathiazole compounds.

| Cancer panel/cell line | Imidazothiazole-Chalcones (μm) | | | | Di phenyl Chalcones (μm) | Boronic chalcones | | A (μm) | B (μm) | C (μm) |
| --- | --- | --- | --- | --- | --- | --- | --- | --- | --- | --- |
| | 7a | 7e | 7f | 8f | | Mono (μm) | Di (μm) | | | |
| HCT116 | 1.88 | 2.33 | 1.01 | 1.40 | — | 3.9 | 1.5 | — | — | — |
| MCF-7 | 2.02 | 2.24 | 1.25 | 0.76 | 23.5 | — | — | 21.5 | 14.3 | 32.5 |
| MDA-MB-231/ATCC | 2.55 | 2.49 | 2.92 | 0.76 | 28.8 | — | — | 25.8 | 15.9 | 43.2 |
| HOP-92 | 0.24 | 1.05 | — | — | — | — | — | — | — | — |
| IGROV1 | 0.21 | 1.04 | — | — | — | — | — | — | — | — |
| CAKI-1 | 1.20 | 0.04 | — | — | — | — | — | — | — | — |

A = 6-OMe-imidazothiazole
B = 6-CF$_3$-imidazothiazole
C = imidazobenzothiazole

From The Table it is observed that, imidazothiazole linked chalcones have exhibited better anticancer activity than diphenyl chalcones (Food and Chemical Toxicology 44 (2006) 704-713) and boronic chalcones (*Mol Pharmacol* 70:426-433, 2006) for some representative cancer cell lines (HCT116, MCF7, and MDA-MB-231/ATCC). Comparatively, diphenyl and boronic chalcones are very low active. Moreover, for other cancer cell lines also imidazothiazole linked chalcones have showed promising anticancer activity, their mechanism of action is under investigation.

Besides this, the chalcone derivatives of the present invention have shown significant anticancer activity compared to basic individual subunits, i.e., 6-OMe-imidazothiazole, 6-CF$_3$-imidazothiazole and imidazobenzothiazoles as seen in Table-4.

Significance of the Work Carried Out

The imidazothiazole-chalcone hybrids that have been synthesized exhibited significant cytotoxic activity against sixty human tumour cell lines.

Advantages of the Invention

1. The present invention provides new imidazothiazole-chalcone hybrids of general formula A, useful as anticancer agents.
2. It also provides a process for the preparation of novel imidazothiazole-chalcone hybrids of general formula A.

We claim:

1. An imidazothiazole-chalcone compound of A

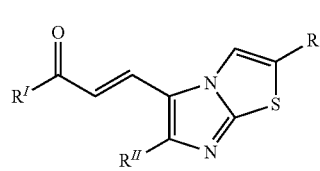

formula A wherein

R = H for 7a-f to 18a-f
R = CH$_3$ for 19a-f to 30a-f

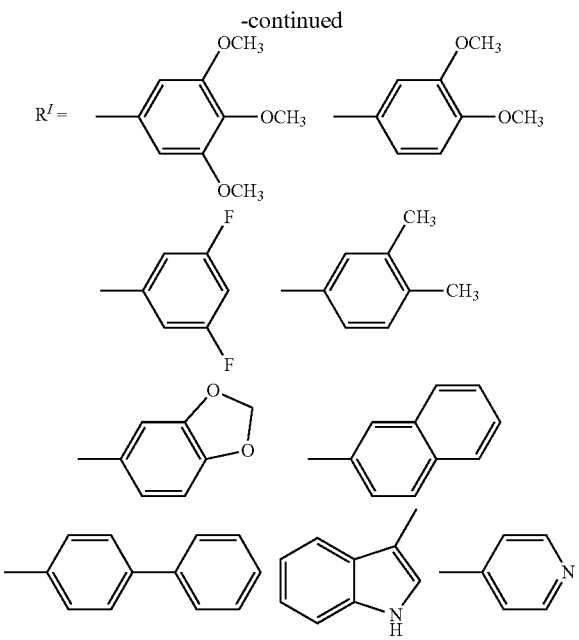

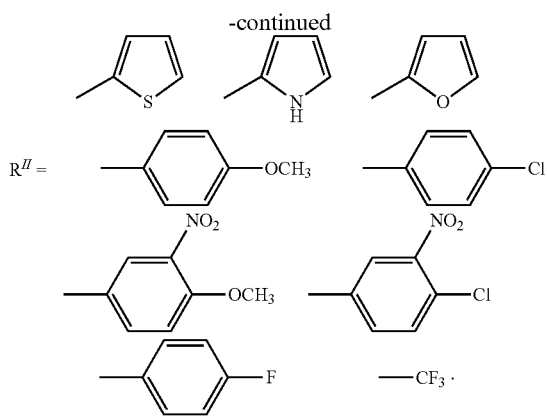

2. An imidazothiazole-chalcone compound chosen from:
(E)-3-(6-(4-methoxyphenyl)imidazo[2,1-b]thiazol-5-yl)-1-(3,4,5-trimethoxyphenyl) prop-2-en-1-one; (7a)
(E)-3-(6-(4-chlorophenyl)imidazo[2,1-b]thiazol-5-yl)-1-(3,4,5-trimethoxyphenyl) prop-2-en-1-one; (7b)
(E)-3-(6-(4-methoxy-3-nitrophenyl)imidazo[2,1-b]thiazol-5-yl)-1-(3,4,5-trimethoxy-phenyl) prop-2-en-1-one; (7c)
(E)-3-(6-(4-chloro-3-nitrophenyl)imidazo[2,1-b]thiazol-5-yl)-1-(3,4,5-trimethoxy-phenyl) prop-2-en-1-one; (7d)
(E)-3-(6-(4-fluorophenyl)imidazo[2,1-b]thiazol-5-yl)-1-(3,4,5-trimethoxyphenyl)prop-2-en-1-one; (7e)
(E)-3-(6-(trifluoromethyl)imidazo[2,1-b]thiazol-5-yl)-1-(3,4,5-trimethoxyphenyl)prop-2-en-1-one; (7f)
(E)-3-(6-(4-methoxyphenyl)-2-methylimidazo[2,1-b]thiazol-5-yl)-1-(3,4,5-trimethoxyphenyl)prop-2-en-1-one; (19a)
(E)-3-(6-(4-chlorophenyl)-2-methylimidazo[2,1-b]thiazol-5-yl)-1-(3,4,5-trimethoxyphenyl)prop-2-en-1-one; (19b)
(E)-3-(6-(4-methoxy-3-nitrophenyl)-2-methylimidazo[2,1-b]thiazol-5-yl)-1-(3,4,5-trimethoxyphenyl)prop-2-en-1-one; (19c)
(E)-3-(6-(-(4-chloro-3-nitrophenyl)-2-methylimidazo[2,1-b]thiazol-5-yl)-1-(3,4,5-trimethoxyphenyl)prop-2-en-1-one; (19d)
(E)-3-(6-(4-fluorophenyl)-2-methylimidazo[2,1-b]thiazol-5-yl)-1-(3,4,5-trimethoxyphenyl)prop-2-en-1-one; (19e)
(E)-3-(2-methyl-6-(trifluoromethyl)imidazo[2,1-b]thiazol-5-yl)-1-(3,4,5-trimethoxyphenyl)prop-2-en-1-one; (19f)
(E)-1-(3,4-dimethoxyphenyl)-3-(6-(4-methoxyphenyl)imidazo[2,1-b]thiazol-5-yl)prop-2-en-1-one; (8a)
(E)-3-(6-(4-chlorophenyl)imidazo[2,1-b]thiazol-5-yl)-1-(3,4-dimethoxyphenyl) Prop-2-en-1-one; (8b)
(E)-1-(3,4-dimethoxyphenyl)-3-(6-(4-methoxy-3-nitrophenyl)imidazo[2,1-b]Thiazol-5-yl)prop-2-en-1-one; (8c)
(E)-3-(6-(4-chloro-3-nitrophenyl)imidazo[2,1-b]thiazol-5-yl)-1-(3,4-dimethoxy phenyl)prop-2-en-1-one; (8d)
(E)-1-(3,4-dimethoxyphenyl)-3-(6-(4-fluorophenyl)imidazo[2,1-b]thiazol-5-yl) Prop-2-en-1-one; (8e)
(E)-1-(3,4-dimethoxyphenyl)-3-(6-(trifluoromethyl)imidazo[2,1-b]thiazol-5-yl) Prop-2-en-1-one; (8f)
(E)-1-(3,4-dimethoxyphenyl)-3-(6-(4-methoxyphenyl)-2-methylimidazo[2,1-b]thiazol-5-yl)prop-2-en-1-one; (20a)
(E)-3-(6-(4-chlorophenyl)-2-methylimidazo[2,1-b]thiazol-5-yl)-1-(3,4-dimethoxy phenyl)prop-2-en-1-one; (20b)
(E)-1-(3,4-dimethoxyphenyl)-3-(6-(4-methoxy-3-nitrophenyl)-2-methylimidazo[2, 1-1)]thiazol-5-yl)prop-2-en-1-one; (20c)
(E)-3-(6-(4-chloro-3-nitrophenyl)-2-methylimidazo[2,1-b]thiazol-5-yl)-1-(3,4-dimethoxyphenyl)prop-2-en-1-one; (20d)
(E)-1-(3,4-dimethoxyphenyl)-3-(6-(4-fluorophenyl)-2-methylimidazo[2,1-b]thiazol-5-yl)prop-2-en-1-one; (20e)
(E)-1-(3,4-dimethoxyphenyl)-3-(2-methyl-6-(trifluoromethyl)imidazo[2,1-b]thiazol-5-yl)prop-2-en-1-one; (20f)
(E)-1-(3,4-dimethylphenyl)-3-(6-(4-methoxyphenyl)imidazo[2,1-b]thiazol-5-yl) prop-2-en-1-one; (9a)
(E)-3-(6-(4-chlorophenyl)imidazo[2,1-b]thiazol-5-yl)-1-(3,4-dimethylphenyl) Prop-2-en-1-one; (9b)
(E)-1-(3,4-dimethylphenyl)-3-(6-(4-methoxy-3-nitrophenyl)imidazo[2,1-b]Thiazol-5-yl)prop-2-en-1-one; (9c)
(E)-3-(6-(4-chloro-3-nitrophenyl)imidazo[2,1-b]thiazol-5-yl)-1-(3,4-dimethyl phenyl)prop-2-en-1-one; (9d)
(E)-1-(3,4-dimethylphenyl)-3-(6-(4-fluorophenyl)imidazo[2,1-b]thiazol-5-yl) prop-2-en-1-one; (9e)
(E)-1-(3,4-dimethylphenyl)-3-(6-(trifluoromethyl)imidazo[2,1-b]thiazol-5-yl) prop-2-en-1-one; (9f)
(E)-1-(3,4-dimethylphenyl)-3-(6-(4-methoxyphenyl)-2-methylimidazo[2,1-b]thiazol-5-yl)prop-2-en-1-one; (21a)
(E)-3-(6-(4-chlorophenyl)-2-methylimidazo[2,1-b]thiazol-5-yl)-1-(3,4-dimethyl phenyl)prop-2-en-1-one; (21b)
(E)-1-(3,4-dimethylphenyl)-3-(6-(4-methoxy-3-nitrophenyl)-2-methylimidazo [2,1-b]thiazol-5-yl)prop-2-en-1-one; (21c)
(E)-3-(6-(4-chloro-3-nitrophenyl)-2-methylimidazo[2,1-b]thiazol-5-yl)-1-(3,4-dimethylphenyl)prop-2-en-1-one; (21d)
(E)-1-(3,4-dimethylphenyl)-3-(6-(4-fluorophenyl)-2-methylimidazo[2,1-b]thiazol-5-yl) prop-2-en-1-one; (21e)
(E)-1-(3,4-dimethylphenyl)-3-(2-methyl-6-(trifluoromethyl)imidazo[2,1-b]thiazol-5-yl)prop-2-en-1-one; (21f)
(E)-1(3,5-difluorophenyl)-3-(6-(4-methoxyphenyl)imidazo[2,1-b]thiazo-5-yl) prop-2-en-1-one; (10a)
(E)-3-(6-(4-chlorophenyl)imidazo[2,1-b]thiazol-5-yl)-1-(3,5-difluorophenyl) prop-2-en-1-one; (10b)
(E)-1-(3,5-difluorophenyl)-3-(6-(4-methoxy-3-nitrophenyl)imidazo[2,1-b]thiazol-5-yl)prop-2-en-1-one; (10c)
(E)-3-(6-(4-chloro-3-nitrophenyl)imidazo[2,1-b]thiazol-5-yl)-1-(3,5-difluorophenyl)prop-2-en-1-one; (10d)
(E)-1-(3,5-difluorophenyl)-3-(6-(4-fluorophenyl)imidazo[2,1-b]thiazol-5-yl)prop-2-en-1-one; (10e)
(E)-1-(3,5-difluorophenyl)-3-(6-(trifluoromethyl)imidazo[2,1-b]thiazol-5-yl)prop-2-en-1-one; (10f)
(E)-1-(3,5-difluorophenyl)-3-(6-(4-methoxyphenyl)-2-methylimidazo[2,1-b]thiazol-5-yl)prop-2-en-1-one; (22a)
(E)-3-(6-(4-chlorophenyl)-2-methylimidazo[2,1-b thiazol-5-yl)-1-(3,5-difluoro phenyl)prop-2-en-1-one; (22b)
(E)-1-(3,5-difluorophenyl)-3-(6-(4-methoxy-3-nitrophenyl)-2-methylimidazo[2,1-b]thiazol-5-yl)prop-2-en-1-one; (22c)

(E)-3-(6-(4-chloro-3-nitrophenyl)-2-methylimidazo[2,1-b]thiazol-5-yl)-1-(3,5-difluoro phenyl)prop-2-en-1-one; (22d)
(E)-1-(3,5-difluorophenyl)-3-(6-(4-fluorophenyl)-2-methylimidazo[2,1-b]thiazol-5-yl)prop-2-en-1-one; (22e)
(E)-1-(3,5-difluorophenyl)-3-(2-methyl-6-(trifluoromethyl)imidazo[2,1-b]thiazol-5-yl)prop-2-en-1-one; (22f)
(E)-1-(benzo[d][1,3]dioxol-5-yl)-3-(6-(4-methoxyphenyl)imidazo[2,1-b]thiazol-5-yl)prop-2-en-1-one; (11a)
(E)-1-(benzo[d][1,3]dioxol-5-yl)-3-(6-(4-chlorophenyl)imidazo[2,1-b]thiazol-5-yl)prop-2-en-1-one; (11b)
(E)-1-(benzo[d][1,3]dioxol-5-yl)-3-(6-(4-methoxy-3-nitrophenyl)imidazo[2,1-b]thiazol-5-yl)prop-2-en-1-one; (11c)
(E)-1-(benzo[d][1,3]dioxol-5-yl)-3-(6-(4-chloro-3-nitrophenyl)imidazo[2,1-b]thiazol-5-yl)prop-2-en-1-one; (11d)
(E)-1-(benzo[d][1,3]dioxol-5-yl)-3-(6-(4-fluorophenyl)imidazo[2,1-b]thiazol-5-yl)prop-2-en-1-one; (11e)
(E)-1-(benzo[d][1,3]dioxol-5-yl)-3-(6-(trifluoromethyl)imidazo[2,1-b]thiazol-5-yl)prop-2-en-1-one; (11f)
(E)-1-(benzo[d][1,3]dioxol-5-yl)-3-(6-(4-methoxyphenyl)-2-methylimidazo[2,1-b]thiazol-5-yl)prop-2-en-1-one; (23a)
(E)-1-(benzo[d][1,3]dioxol-5-yl)-3-(6-(4-chlorophenyl)-2-methylimidazo[2,1-b]thiazol-5-yl)prop-2-en-1-one; (23b)
(E)-1-(benzo[d][1,3]dioxol-5-yl)-3-(6-(4-methoxy-3-nitrophenyl)-2-methylimidazo [2,1-b]thiazol-5-yl)prop-2-en-1-one; (23c)
(E)-1-(benzo[d][1,3]dioxol-5-yl)-3-(6-(4-chloro-3-nitrophenyl)-2-methylimidazo[2,1-b]thiazol-5-yl)prop-2-en-1-one; (23d)
(E)-1-(benzo[d][1,3]dioxol-5-yl)-3-(6-(4-fluorophenyl)-2-methylimidazo[2,1-b]thiazol-5-yl)prop-2-en-1-one; (23e)
(E)-1-(benzo[d][1,3]dioxol-5-yl)-3-(2-methyl-6-(trifluoromethyl)imidazo[2,1-b]thiazol-5-yl)prop-2-en-1-one; (23f)
(E)-3-(6-(4-methoxyphenyl)imidazo[2,1-b]thiazol-5-yl)-1-(naphthalen-2-yl) prop-2-en-1-one; (12a)
(E)-3-(6-(4-chlorophenyl)imidazo[2,1-b]thiazol-5-yl)-1-(naphthalen-2-yl) prop-2-en-1-one; (12b)
(E)-3-(6-(4-methoxy-3-nitrophenyl)imidazo[2,1-b]thiazol-5-yl)-1-(naphthalen-2-yl)prop-2-en-1-one; (12c)
(E)-3-(6-(4-chloro-3-nitrophenyl)imidazo[2,1-b]thiazol-5-yl)-1-(naphthalen-2-yl)prop-2-en-1-one; (12d)
(E)-3-(6-(4-fluorophenyl)imidazo[2,1-b]thiazol-5-yl)-1-(naphthalen-2-yl)prop-2-en-1-one; (12e)
(E)-1-(naphthalen-2-yl)-3-(6-(trifluoromethyl)imidazo[2,1-b]thiazol-5-yl)prop-2-en-1-one; (12f)
(E)-3-(6-(4-methoxyphenyl)-2-methylimidazo[2,1-b]thiazol-5-yl)-1-(naphthalen-2-yl) prop-2-en-1-one; (24a)
(E)-3-(6-(4-chlorophenyl)-2-methylimidazo[2,1-b]thiazol-5-yl)-1-(naphthalen-2-yl)prop-2-en-1-one; (24b)
(E)-3-(6-(4-methoxy-3-nitrophenyl)-2-methylimidazo[2,1-b]thiazol-5-yl)-1-(naphthalen-2-yl)prop-2-en-1-one; (24c)
(E)-3-(6-(4-chloro-3-nitrophenyl)-2-methylimidazo[2,1-b]thiazol-5-yl)-1-(naphthalen-2-yl)prop-2-en-1-one; (24d)
(E)-3-(6-(4-fluorophenyl)-2-methylimidazo[2,1-b]thiazol-5-yl)-1-(naphthalen-2-yl)prop-2-en-1-one; (24e)
(E)-3-(2-methyl-6-(trifluoromethyl)imidazo[2,1-b]thiazol-5-yl)-1-(naphthalen-2-yl)prop-2-en-1-one; (24f)
(E)-1-(biphenyl-4-yl)-3-(6-(4-methoxyphenyl)imidazo[2,1-b]thiazol-5-yl)prop-2-en-1-one; (13a)
(E)-1-(biphenyl-4-yl)-3-(6-(4-chlorophenyl)imidazo[2,1-b]thiazol-5-yl)prop-2-en-1-one; (13b)
(E)-1-(biphenyl-4-yl)-3-(6-(4-methoxy-3-nitrophenyl)imidazo[2,1-b]thiazol-5-yl)prop-2-en-1-one; (13c)
(E)-1-(biphenyl-4-yl)-3-(6-(4-chloro-3-nitrophenyl)imidazo[2,1-b]thiazol-5-yl)prop-2-en-1-one; (13d)
(E)-1-(biphenyl-4-yl)-3-(6-(4-fluorophenyl)imidazo[2,1-b]thiazol-5-yl)prop-2-en-1-one; (13e)
(E)-1-(biphenyl-4-yl)-3-(6-(trifluoromethyl)imidazo[2,1-b]thiazol-5-yl)prop-2-en-1-one; (13f)
(E)-1-(biphenyl-4-yl)-3-(6-(4-methoxyphenyl)-2-methylimidazo[2,1-b]thiazol-5-yl)prop-2-en-1-one; (25a)
(E)-1-(biphenyl-4-yl)-3-(6-(4-chlorophenyl)-2-methyl imidazo[2,1-b]thiazol-5-yl)prop-2-en-1-one; (25b)
(E)-1-(biphenyl-4-yl)-3-(6-(4-methoxy-3-nitrophenyl)-2-methylimidazo[2,1-b]thiazol-5-yl)prop-2-en-1-one; (25c)
(E)-1-(biphenyl-4-yl)-3-(6-(4-chloro-3-nitrophenyl)-2-methyl imidazo[2,1-b]thiazol-5-yl)prop-2-en-1-one; (25d)
(E)-1-(biphenyl-4-yl)-3-(6-(4-fluorophenyl)-2-methylimidazo[2,1-b]thiazol-5-yl)prop-2-en-1-one; (25e)
(E)-1-(biphenyl-4-yl)-3-(2-methyl-6-(trifluoromethyl)imidazo[2,1-b]thiazol-5-yl)prop-2-en-1-one; (25f)
(E)-3-(6-(4-methoxyphenyl)imidazo[2,1-b]thiazol-5-yl)-1-(pyridin-4-yl)prop-2-en-1-one; (14a)
(E)-3-(6-(4-chlorophenyl)imidazo[2,1-b]thiazol-5-yl)-1-(pyridin-4-yl)prop-2-en-1-one; (14b)
(E)-3-(6-(4-methoxy-3-nitrophenyl)imidazo[2,1-b]thiazol-5-yl)-1-(pyridin-4-yl)prop-2-en-1-one; (14c)
(E)-3-(6-(4-chloro-3-nitrophenyl)imidazo[2,1-b]thiazol-5-yl)-1-(pyridin-4-yl)prop-2-en-1-one; (14d)
(E)-3-(6-(4-fluorophenyl)imidazo[2,1-b]thiazol-5-yl)-1-(pyridin-4-yl)prop-2-en-1-one; (14e)
(E)-1-(pyridin-4-yl)-3-(6-(trifluoromethyl)imidazo[2,1-b]thiazol-5-yl)prop-2-en-1-one; (14f)
(E)-3-(6-(4-methoxyphenyl)-2-methylimidazo[2,1-b]thiazol-5-yl)-1-(pyridin-4-yl)prop-2-en-1-one; (26a)
(E)-3-(6-(4-chlorophenyl)-2-methylimidazo[2,1-b]thiazol-5-yl)-1-(pyridin-4-yl)prop-2-en-1-one; (26b)
(E)-3-(6-(4-methoxy-3-nitrophenyl)-2-methylimidazo[2,1-b]thiazol-5-yl)-1-(pyridin-4-yl)prop-2-en-1-one; (26c)
(E)-3-(6-(4-chloro-3-nitrophenyl)-2-methylimidazo[2,1-b]thiazol-5-yl)-1-(pyridin-4-yl)prop-2-en-1-one; (26d)
(E)-3-(6-(4-fluorophenyl)-2-methylimidazo[2,1-b]thiazol-5-yl)-1-(pyridin-4-yl)prop-2-en-1-one; (26e)
(E)-3-(2-methyl-6-(trifluoromethyl)imidazo[2,1-b]thiazol-5-yl)-1-(pyridin-4-yl)prop-2-en-1-one; (26f)
(E)-1-(1H-indol-3-yl)-3-(6-(4-methoxyphenyl)imidazo[2,1-b]thiazol-5-yl)prop-2-en-1-one; (15a)
(E)-3-(6-(4-chlorophenyl)imidazo[2,1-b]thiazol-5-yl)-1-(1H-indol-3-yl)prop-2-en-1-one; (15b)
(E)-1-(1H-indol-3-yl)-3-(6-(4-methoxy-3-nitrophenyl)imidazo[2,1-b]thiazol-5-yl)prop-2-en-1-one; (15c)
(E)-3-(6-(4-chloro-3-nitrophenyl)imidazo[2,1-b]thiazol-5-yl)-1-(1H-indol-3-yl)prop-2-en-1-one; (15d)
(E)-3-(6-(4-fluorophenyl)imidazo[2,1-b]thiazol-5-yl)-1-(1H-indol-3-yl)prop-2-en-1-one; (15e)
(E)-1-(1H-indol-3-yl)-3-(6-(trifluoromethyl)imidazo[2,1-b]thiazol-5-yl)prop-2-en-1-one; (15f)
(E)-1-(1H-indol-3-yl)-3-(6-(4-methoxyphenyl)-2-methyl imidazo[2,1-b]thiazol-5-yl)prop-2-en-1-one; (27a)
(E)-3-(6-(4-chlorophenyl)-2-methylimidazo[2,1-b]thiazol-5-yl)-1-(1H-indol-3-yl)prop-2-en-1-one; (27b)

(E)-1-(1H-indol-3-yl)-3-(6-(4-methoxy-3-nitrophenyl)-2-methylimidazo[2,1-b]thiazol-5-yl)prop-2-en-1-one; (27c)

(E)-3-(6-(4-chloro-3-nitrophenyl)-2-methylimidazo[2,1-b]thiazol-5-yl)-1-(1H-indol-3-yl)prop-2-en-1-one; (27d)

(E)-3-(6-(4-fluorophenyl)-2-methylimidazo[2,1-b]thiazol-5-yl)-1-(1H-indol-3-yl)prop-2-en-1-one; (27e)

(E)-1-(1H-indol-3-yl)-3-(2-methyl-6-(trifluoromethyl)imidazo[2,1-b]thiazol-5-yl)prop-2-en-1-one; (27f)

(E)-3-(6-(4-methoxyphenyl)imidazo[2,1-b]thiazol-5-yl)-1-(thiophen-2-yl)prop-2-en-1-one; (16a)

(E)-3-(6-(4-chlorophenyl)imidazo[2,1-b]thiazol-5-yl)-1-(thiophen-2-yl)prop-2-en-1-one; (16b)

(E)-3-(6-(4-methoxy-3-nitrophenyl)imidazo[2,1-b]thiazol-5-yl)-1-(thiophen-2-yl)prop-2-en-1-one; (16c)

(E)-3-(6-(4-chloro-3-nitrophenyl)imidazo[2,1-b]thiazol-5-yl)-1-(thiophen-2-yl)prop-2-en-1-one; (16d)

(E)-3-(6-(4-fluorophenyl)imidazo[2,1-b]thiazol-5-yl)-1-(thiophen-2-yl)prop-2-en-1-one; (16e)

(E)-1-(thiophen-2-yl)-3-(6-(trifluoromethyl)imidazo[2,1-b]thiazol-5-yl)prop-2-en-1-one; (16f)

(E)-3-(6-(4-methoxyphenyl)-2-methylimidazo[2,1-b]thiazol-5-yl)-1-(thiophen-2-yl)prop-2-en-1-one; (28a)

(E)-3-(6-(4-chlorophenyl)-2-methylimidazo[2,1-b]thiazol-5-yl)-1-(thiophen-2-yl)prop-2-en-1-one; (28b)

(E)-3-(6-(4-methoxy-3-nitrophenyl)-2-methylimidazo[2,1-b]thiazol-5-yl)-1-(thiophen-2-yl)prop-2-en-1-one; (28c)

(E)-3-(6-(4-chloro-3-nitrophenyl)-2-methylimidazo[2,1-b]thiazol-5-yl)-1-(thiophen-2-yl)prop-2-en-1-one; (28d)

(E)-3-(6-(4-fluorophenyl)-2-methylimidazo[2,1-b]thiazol-5-yl)-1-(thiophen-2-yl)prop-2-en-1-one; (28e)

(E)-3-(2-methyl-6-(trifluoromethyl)imidazo[2,1-b]thiazol-5-yl)-1-(thiophen-2-yl)prop-2-en-1-one; (28f)

(E)-3-(6-(4-methoxyphenyl)imidazo[2,1-b]thiazol-5-yl)-1-(1H-pyrrol-2-yl)prop-2-en-1-one; (17a)

(E)-3-(6-(4-chlorophenyl)imidazo[2,1-b]thiazol-5-yl)-1-(1H-pyrrol-2-yl)prop-2-en-1-one; (17b)

(E)-3-(6-(4-methoxy-3-nitrophenyl)imidazo[2,1-b]thiazol-5-yl)-1-(1H-pyrrol-2-yl)prop-2-en-1-one; (17c)

(E)-3-(6-(4-chloro-3-nitrophenyl)imidazo[2,1-b]thiazol-5-yl)-1-(1H-pyrrol-2-yl)prop-2-en-1-one; (17d)

(E)-3-(6-(4-fluorophenyl)imidazo[2,1-b]thiazol-5-yl)-1-(1H-pyrrol-2-yl)prop-2-en-1-one; (17e)

(E)-1-(1H-pyrrol-2-yl)-3-(6-(trifluoromethyl)imidazo[2,1-b]thiazol-5-yl)prop-2-en-1-one; (17f)

(E)-3-(6-(4-methoxyphenyl)-2-methylimidazo[2,1-b]thiazol-5-yl)-1-(1H-pyrrol-2-yl)prop-2-en-1-one; (29a)

(E)-3-(6-(4-chlorophenyl)-2-methylimidazo[2,1-b]thiazol-5-yl)-1-(1H-pyrrol-2-yl)prop-2-en-1-one; (29b)

(E)-3-(6-(4-methoxy-3-nitrophenyl)-2-methylimidazo[2,1-b]thiazol-5-yl)-1-(1H-pyrrol-2-yl)prop-2-en-1-one; (29c)

(E)-3-(6-(4-chloro-3-nitrophenyl)-2-methylimidazo[2,1-b]thiazol-5-yl)-1-(1H-pyrrol-2-yl)prop-2-en-1-one; (29d)

(E)-3-(6-(4-fluorophenyl)-2-methylimidazo[2,1-b]thiazol-5-yl)-1-(1H-pyrrol-2-yl)prop-2-en-1-one; (29e)

(E)-3-(2-methyl-6-(trifluoromethyl)imidazo[2,1-b]thiazol-5-yl)-1-(1H-pyrrol-2-yl)prop-2-en-1-one; (29f)

(E)-1-(furan-2-yl)-3-(6-(4-methoxyphenyl)imidazo[2,1-b]thiazol-5-yl)prop-2-en-1-one; (18a)

(E)-3-(6-(4-chlorophenyl)imidazo[2,1-b]thiazol-5-yl)-1-(furan-2-yl)prop-2-en-1-one; (18b)

(E)-1-(furan-2-yl)-3-(6-(4-methoxy-3-nitrophenyl)imidazo[2,1-b]thiazol-5-yl)prop-2-en-1-one; (18c)

(E)-3-(6-(4-chloro-3-nitrophenyl)imidazo[2,1-b]thiazol-5-yl)-1-(furan-2-yl)prop-2-en-1-one; (18d)

(E)-1-(furan-2-yl)-3-(6-(4-fluorophenyl)imidazo[2,1-b]thiazol-5-yl)prop-2-en-1-one; (18e)

(E)-1-(furan-2-yl)-3-(6-(trifluoromethyl)imidazo[2,1-b]thiazol-5-yl)prop-2-en-1-one; (18f)

(E)-1-(furan-2-yl)-3-(6-(4-methoxyphenyl)-2-methylimidazo[2,1-b]thiazol-5-yl)prop-2-en-1-one; (30a)

(E)-3-(6-(4-chlorophenyl)-2-methylimidazo[2,1-b]thiazol-5-yl)-1-(furan-2-yl)prop-2-en-1-one; (30b)

(E)-1-(furan-2-yl)-3-(6-(4-methoxy-3-nitrophenyl)-2-methylimidazo[2,1-b]thiazol-5-yl)prop-2-en-1-one; (30c)

(E)-3-(6-(4-chloro-3-nitrophenyl)-2-methylimidazo[2,1-b]thiazol-5-yl)-1-(furan-2-yl)prop-2-en-1-one; (30d)

(E)-3-(6-(4-fluorophenyl)-2-methylimidazo[2,1-b]thiazol-5-yl)-1-(furan-2-yl)prop-2-en-1-one; (30e)

(E)-1-(furan-2-yl)-3-(2-methyl-6-(trifluoromethyl)imidazo[2,1-b]thiazol-5-yl)prop-2-en-1-one; (30f).

3. An imidazothiazole-chalcone compound chosen from:

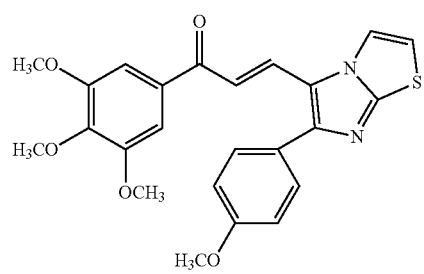

7a

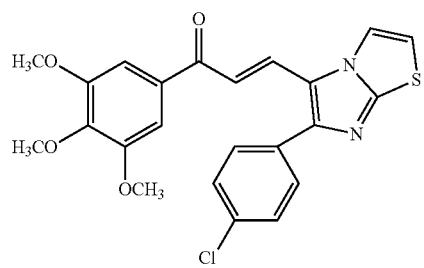

7b

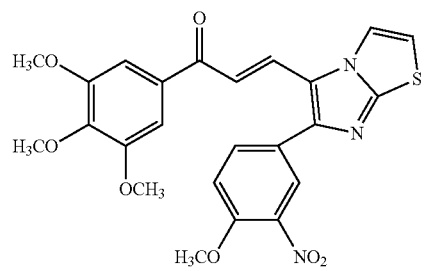

7c

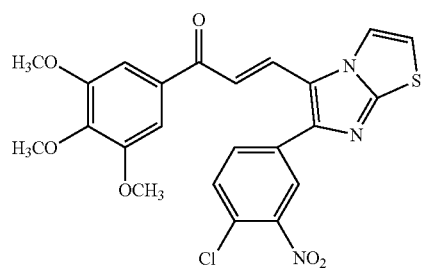

7d

-continued
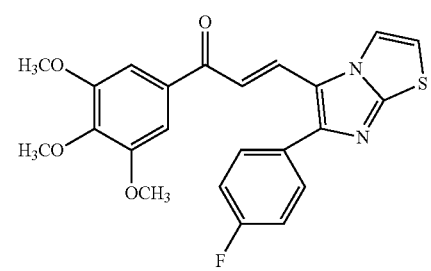
7e
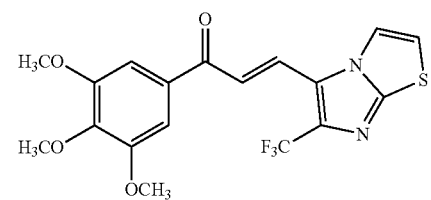
7f
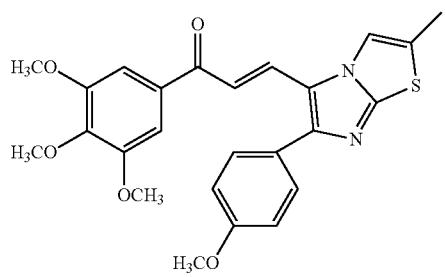
19a
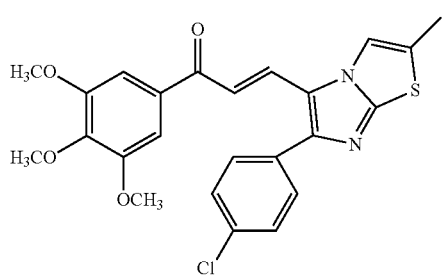
19b
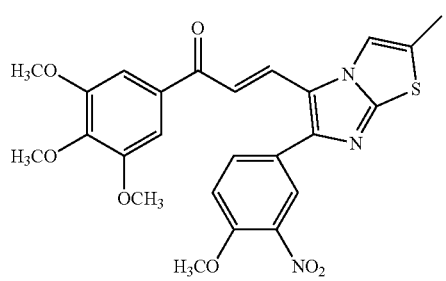
19c
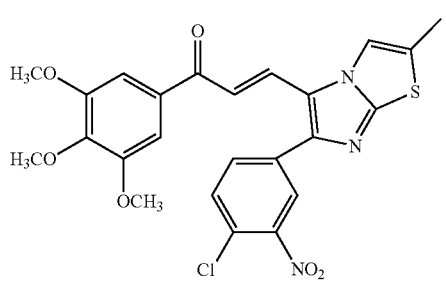
19d
-continued
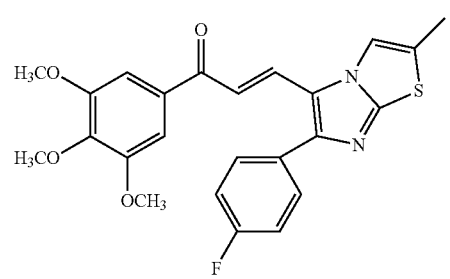
19e
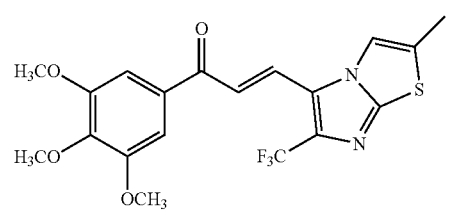
19f
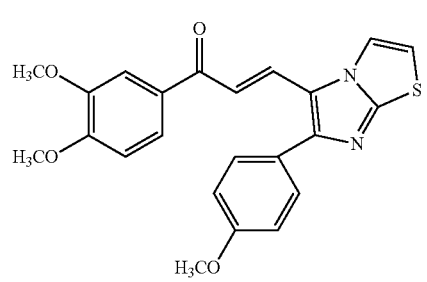
8a
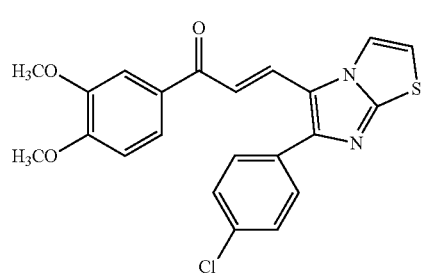
8b
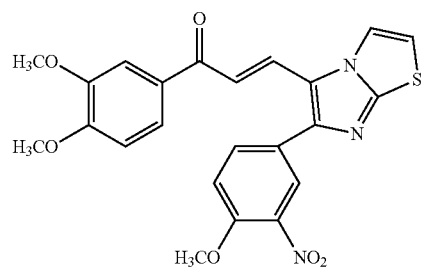
8c
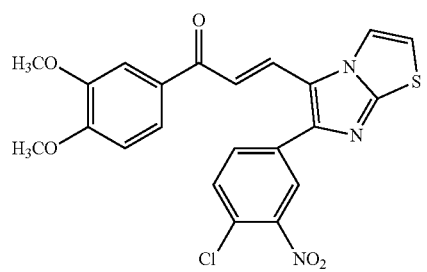
8d 8e
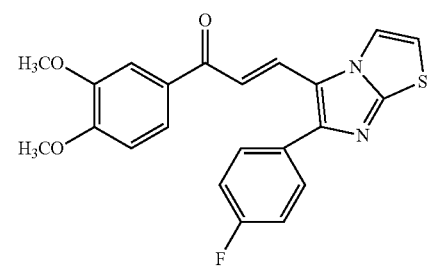
8f
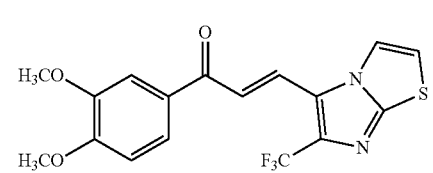
20a
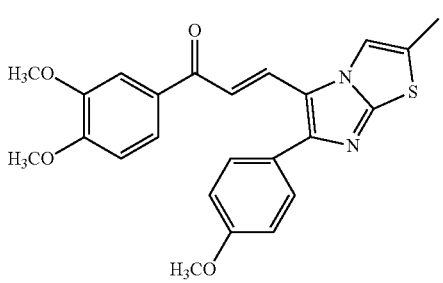
20b
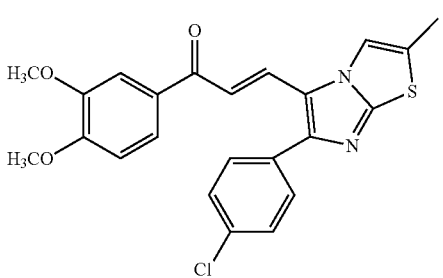
20c
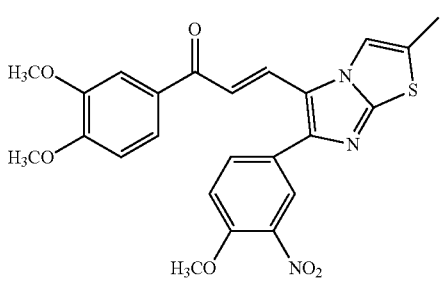
20d
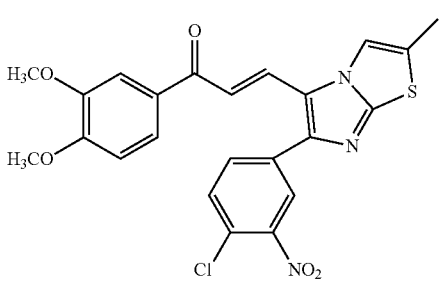
20e
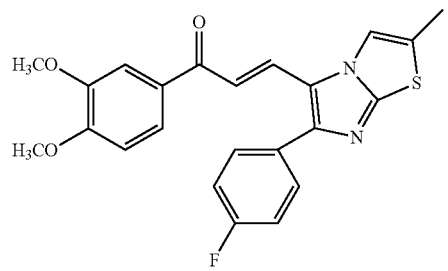
20f
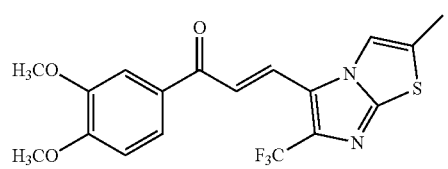
9a
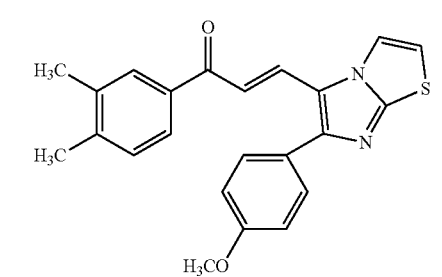
9b
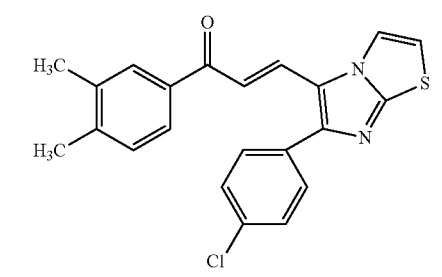
9c
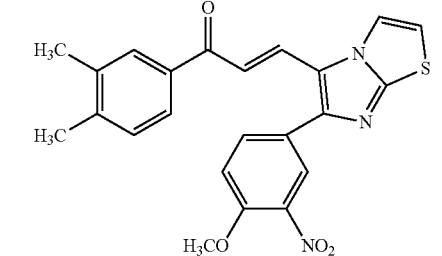
9d
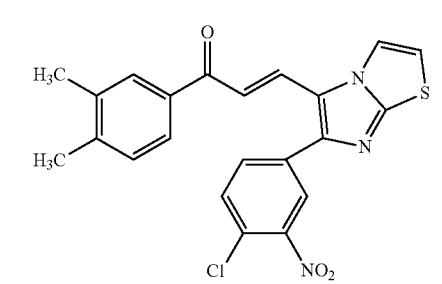

9e 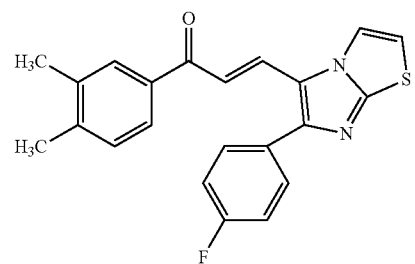
9f 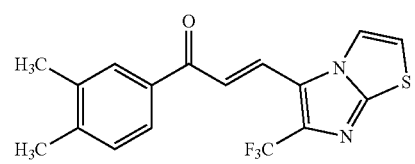
21a 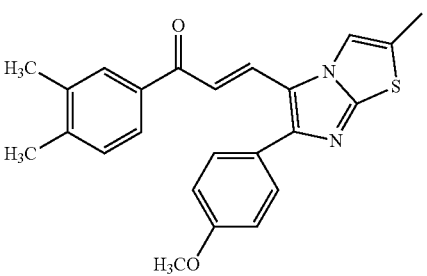
21b 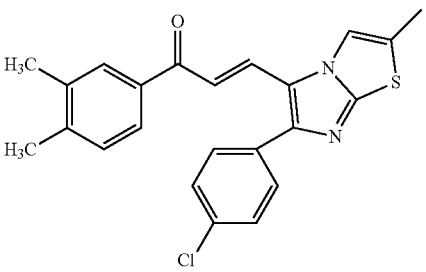
21c 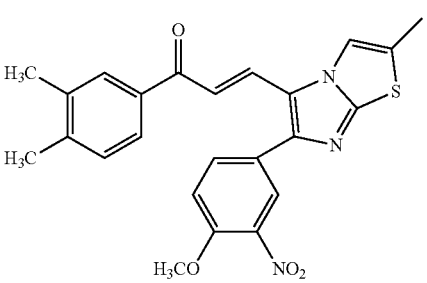
21d 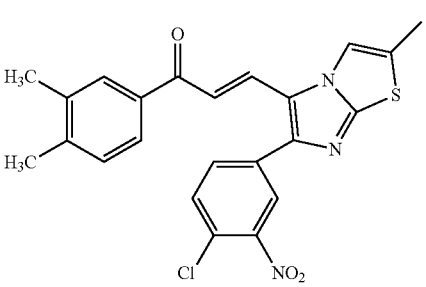
21e 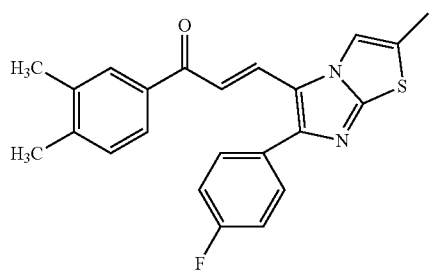
21f 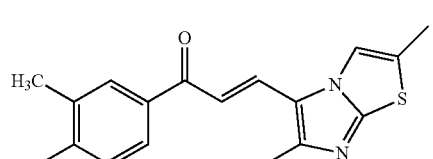
10a 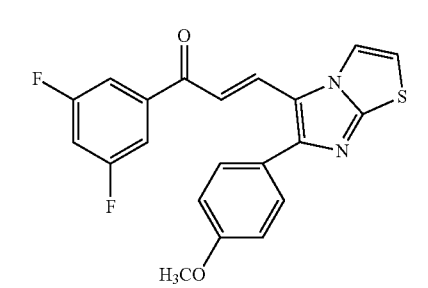
10b 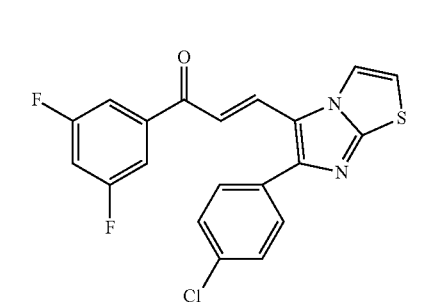
10c 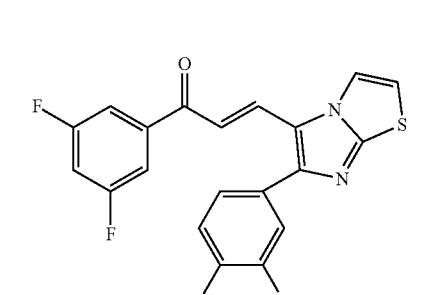
10d 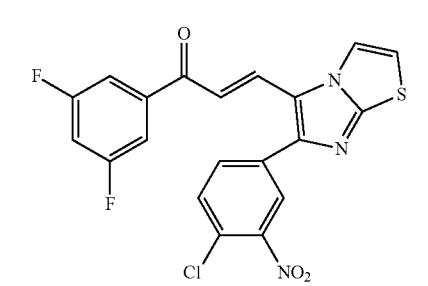

10e 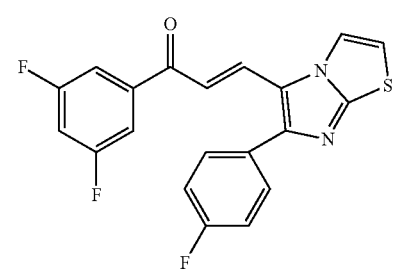
10f 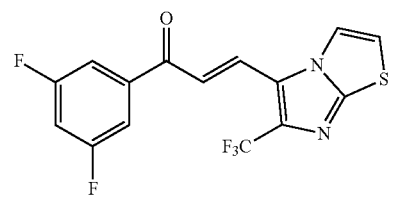
22a 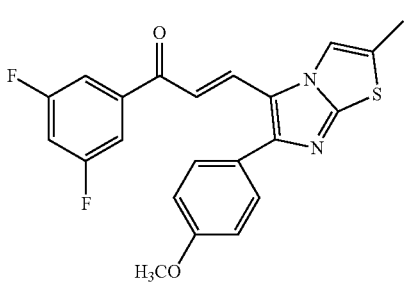
22b 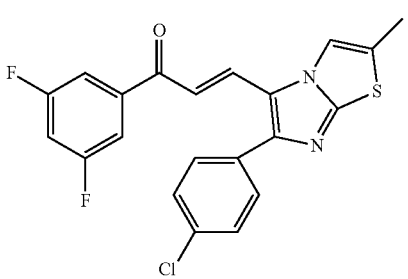
22c 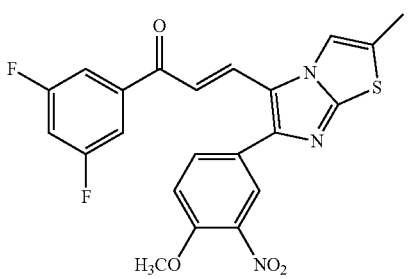
22d 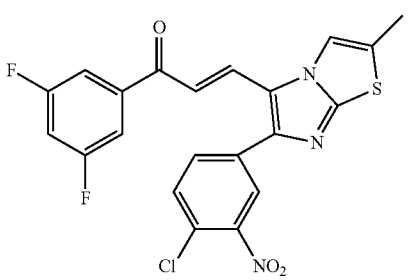
22e 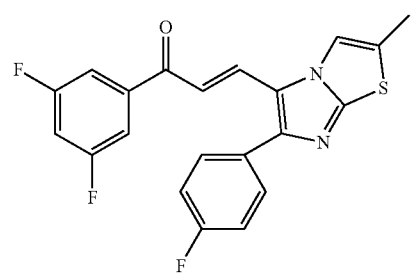
22f 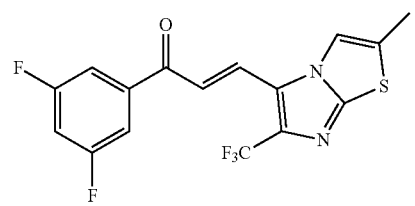
11a 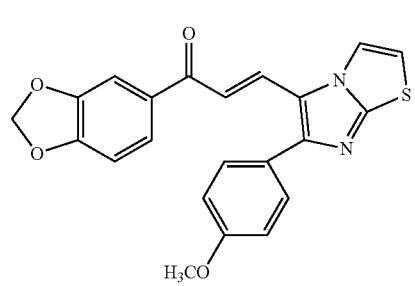
11b 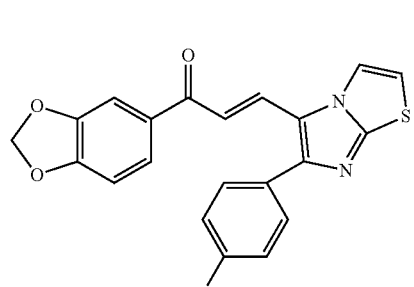
11c 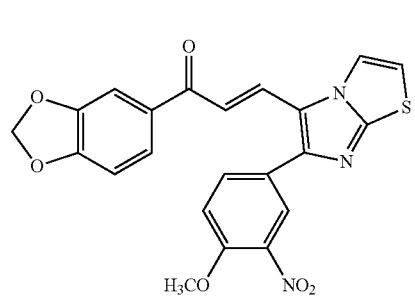
11d 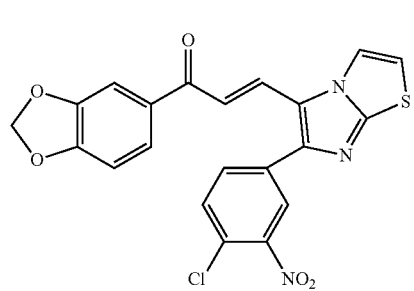

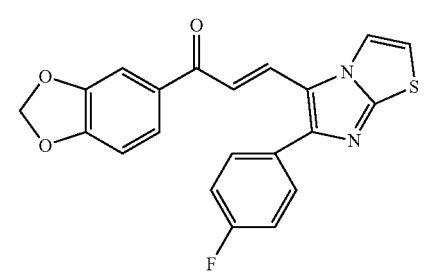
11e
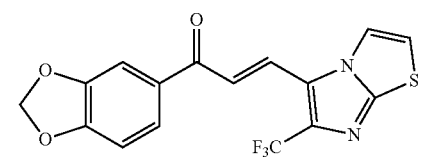
11f
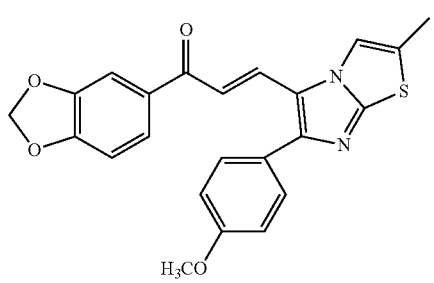
23a
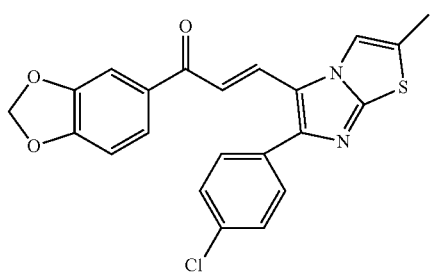
23b
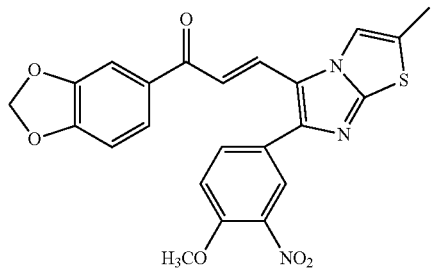
23c
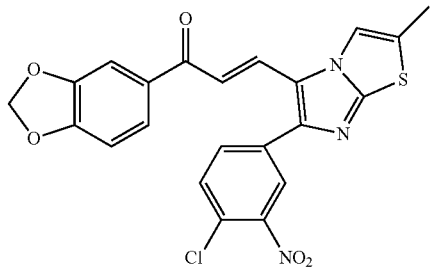
23d
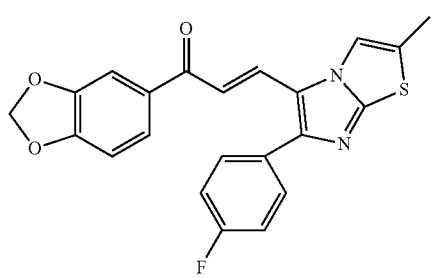
23e
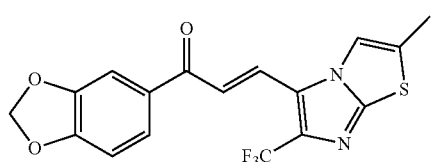
23f
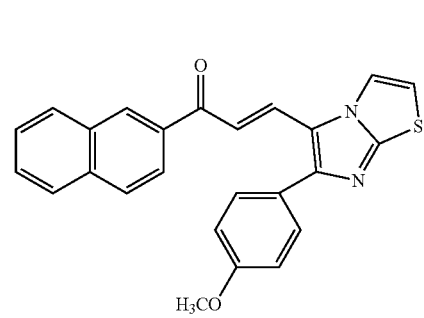
12a
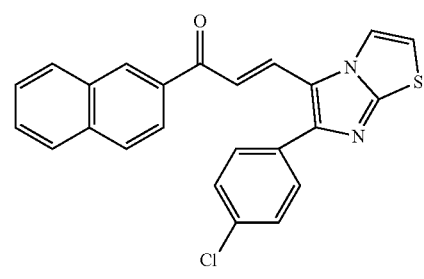
12b
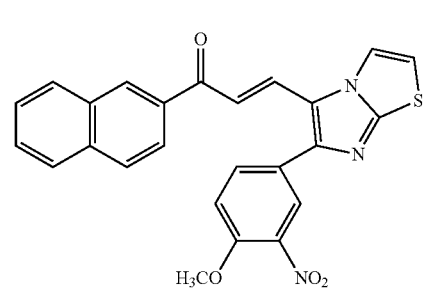
12c
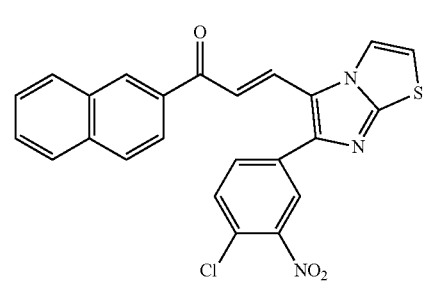
12d

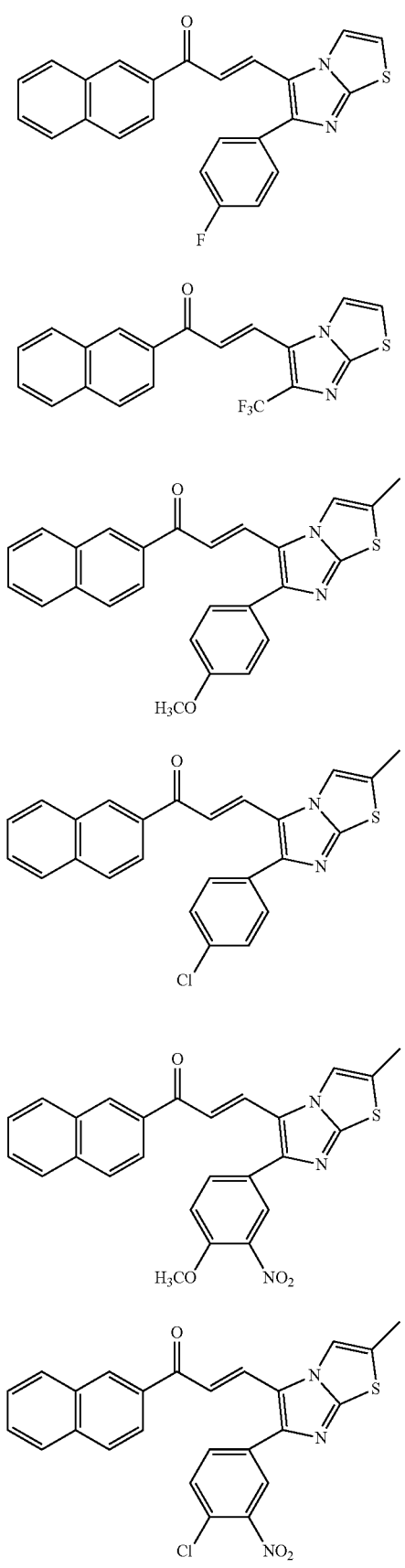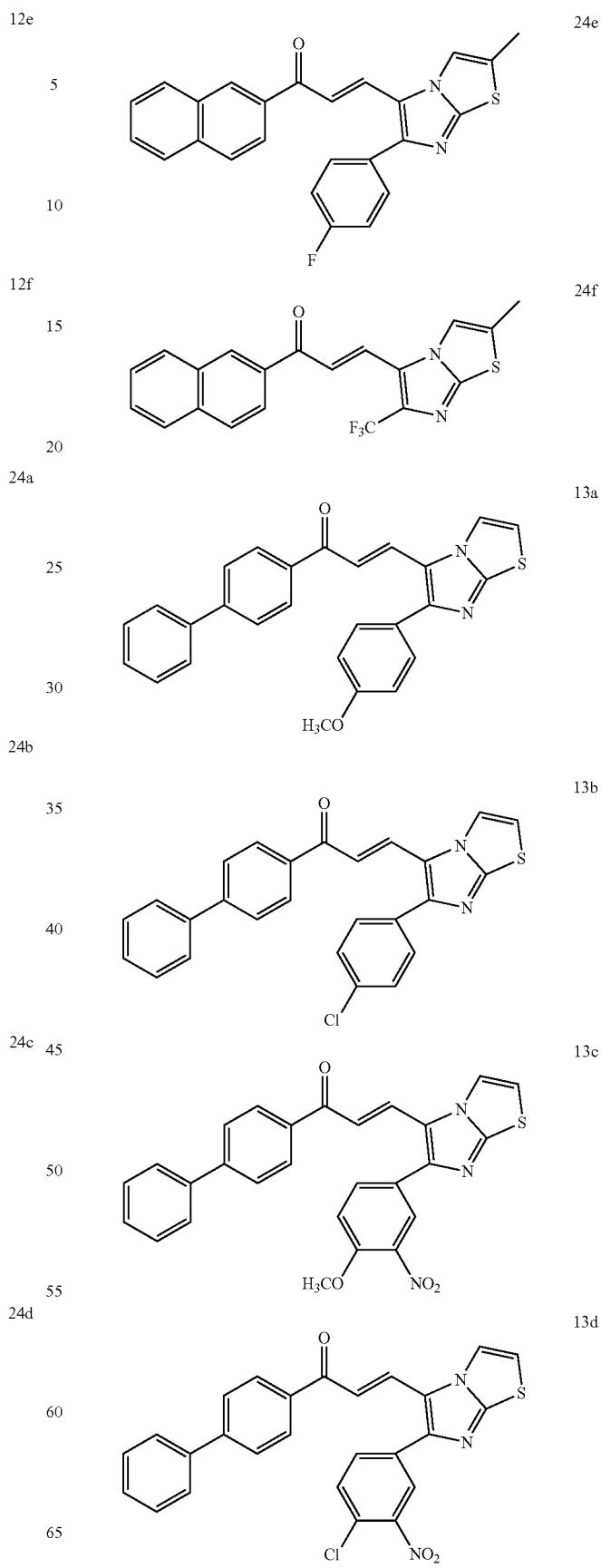

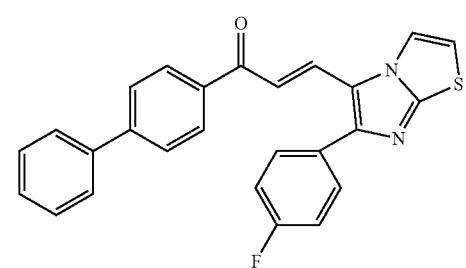
13e
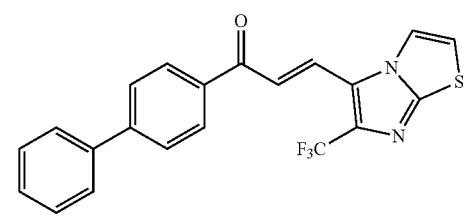
13f
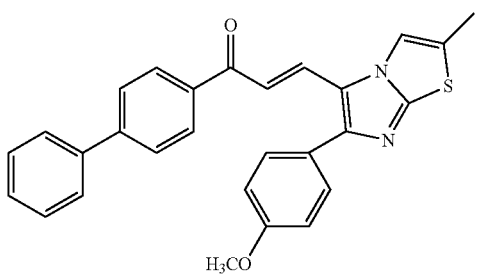
25a
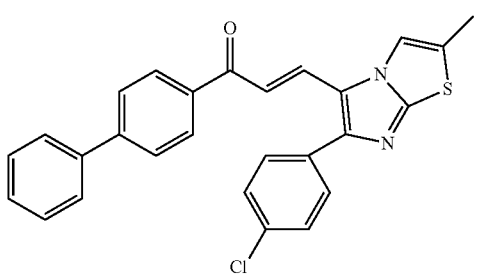
25b
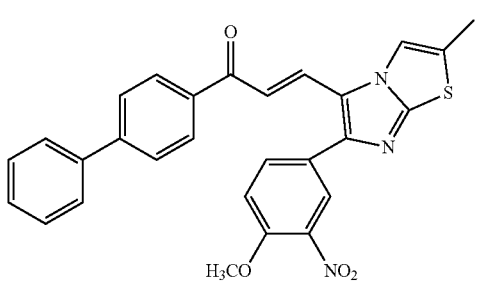
25c
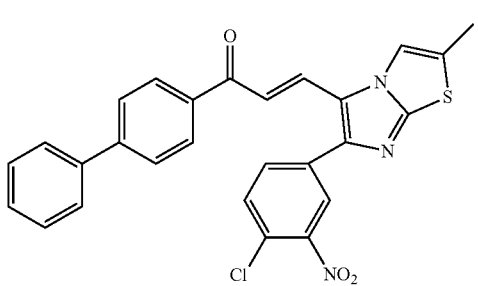
25d
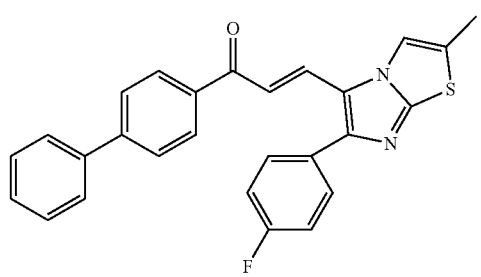
25e
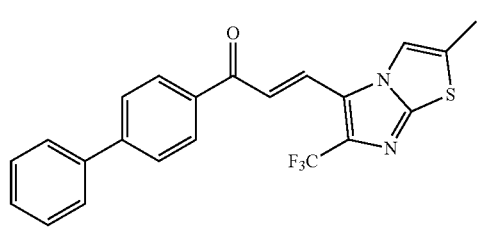
25f
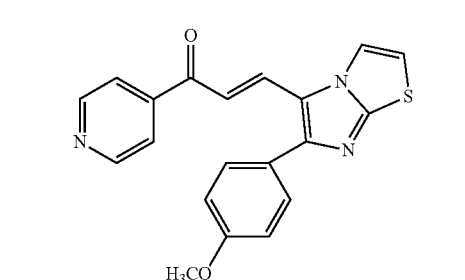
14a
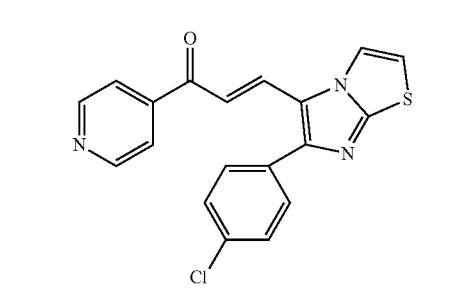
14b
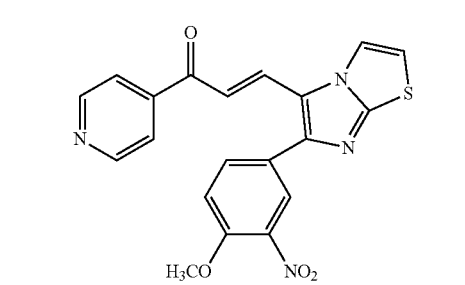
14c
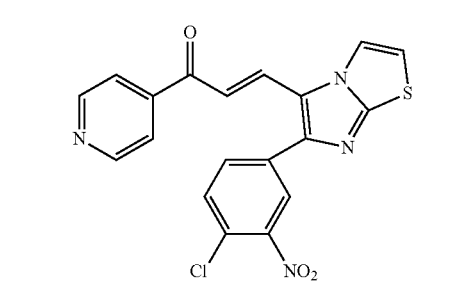
14d

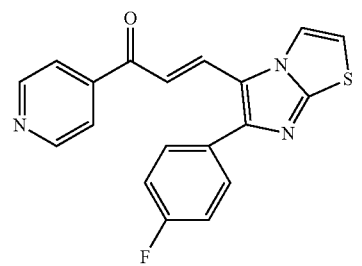
14e
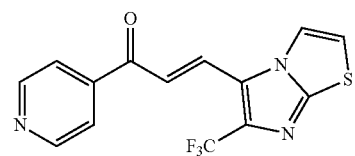
14f
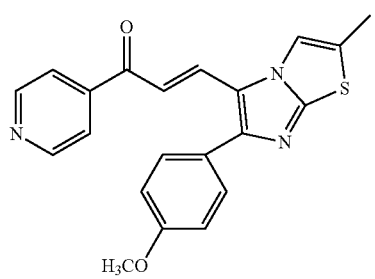
26a
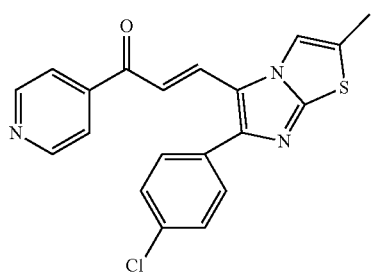
26b
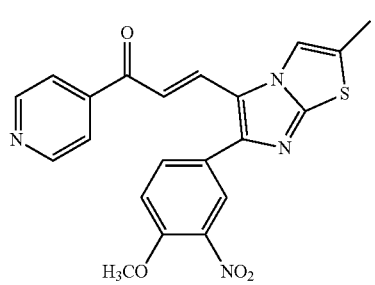
26c
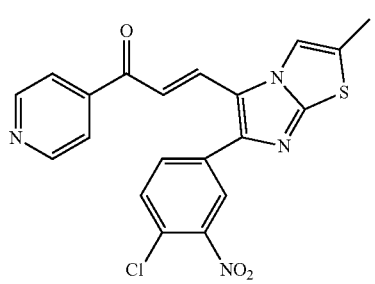
26d
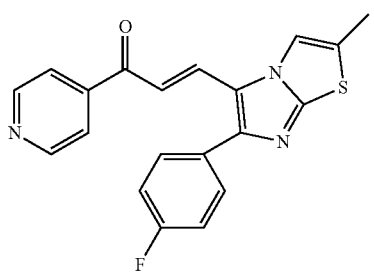
26e
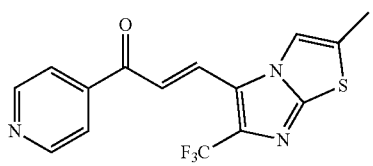
26f
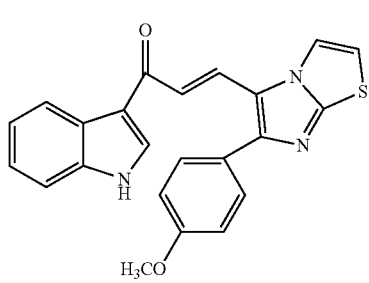
15a
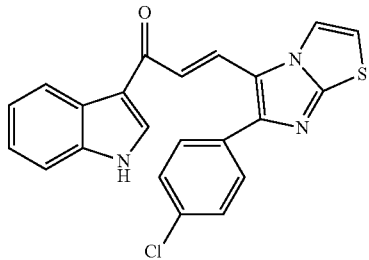
15b
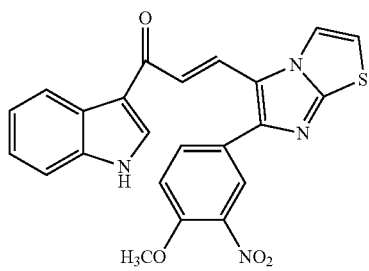
15c
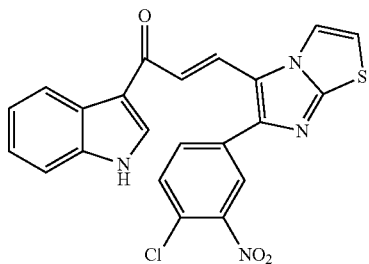
15d

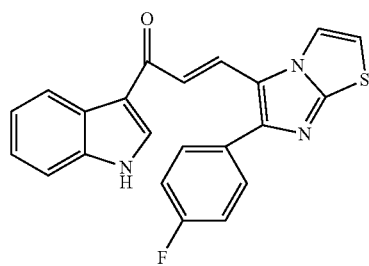 15e
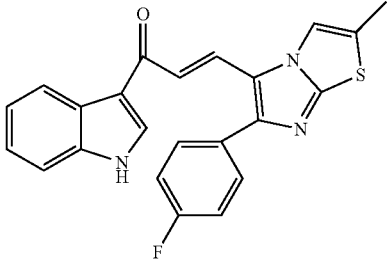 27e
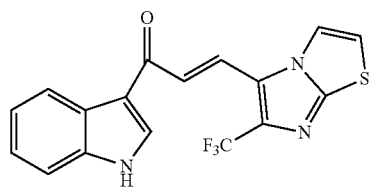 15f
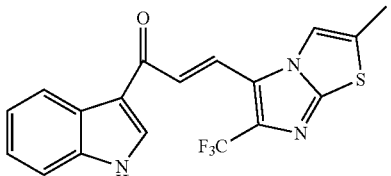 27f
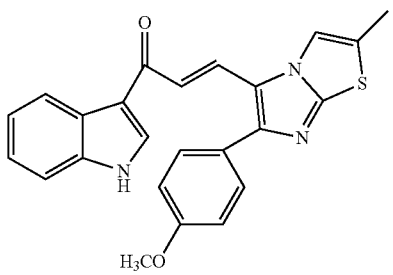 27a
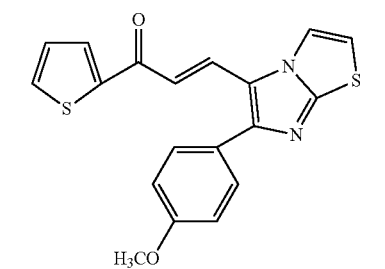 16a
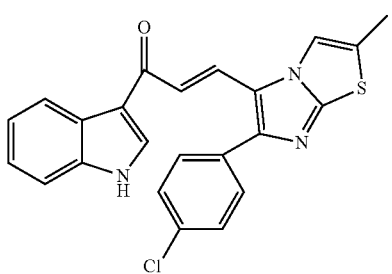 27b
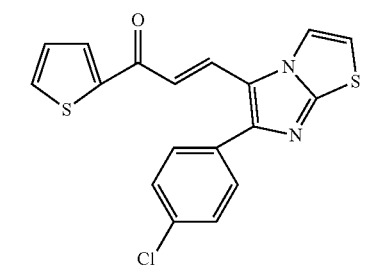 16b
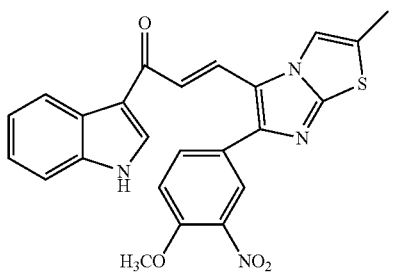 27c
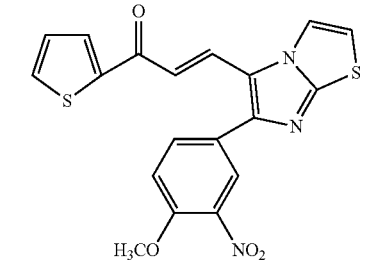 16c
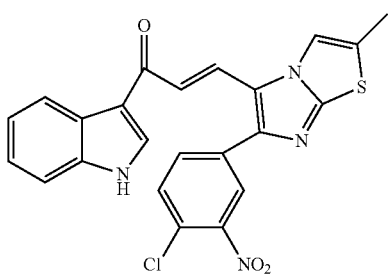 27d
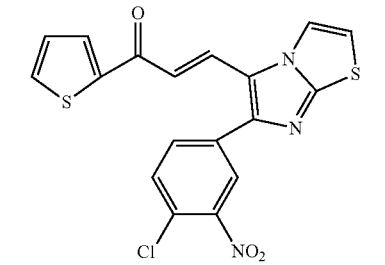 16d 16e 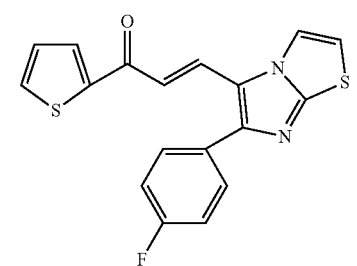
16f 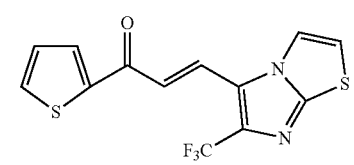
28a 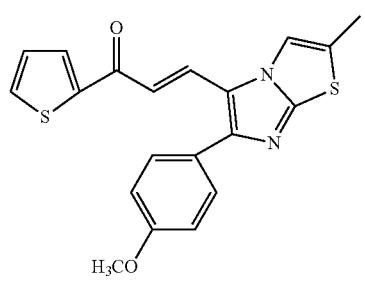
28b 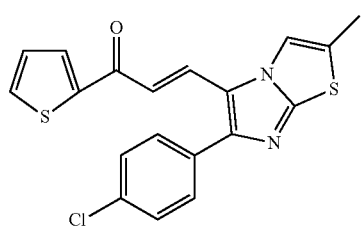
28c 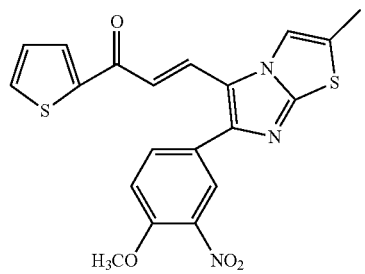
28d 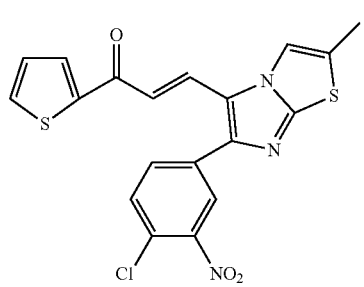
28e 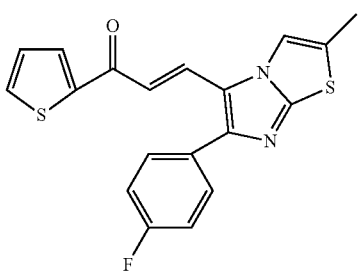
28f 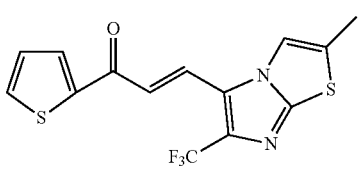
17a 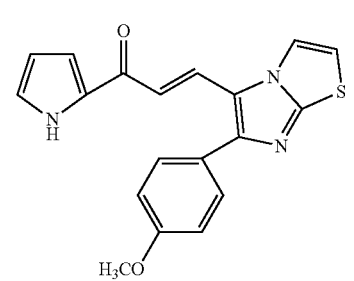
17b 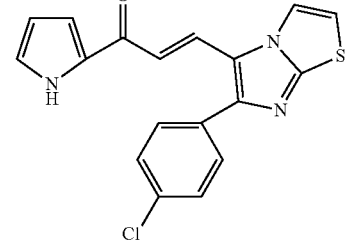
17c 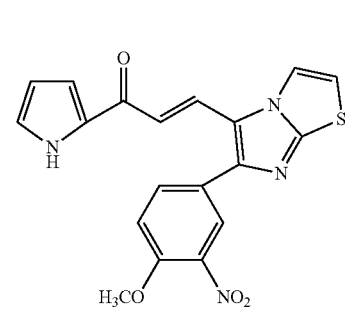
17d 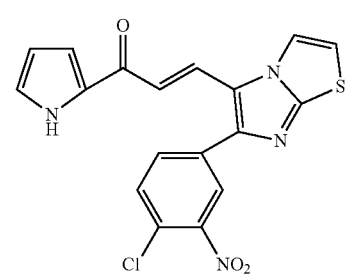

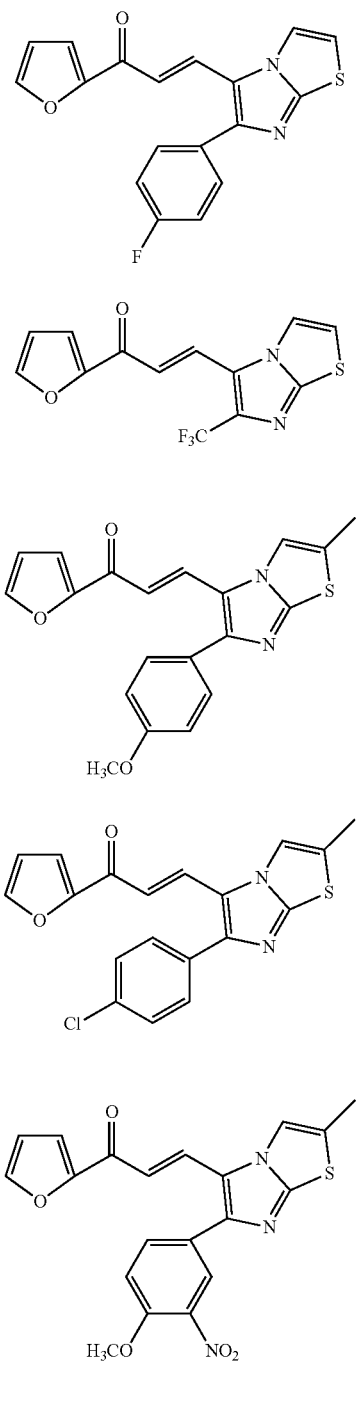

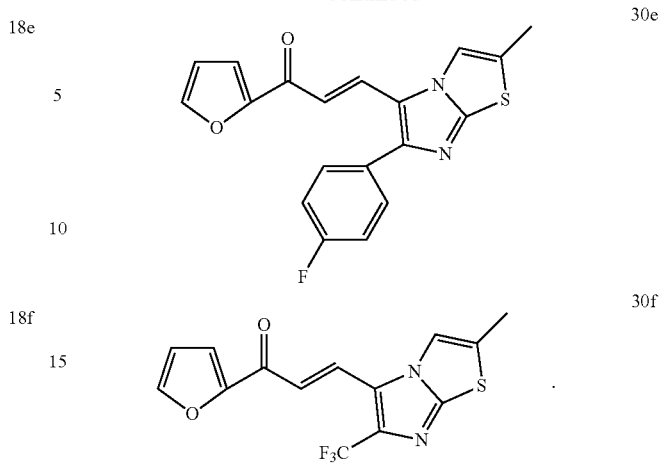

4. The imidazothiazole-chalcone compound of formula 7a, 7e, 7f, 8f and 19e as claimed in claim 2, exhibiting in vitro anticancer activity against human cancer cell lines selected from the group consisting of Leukemia cell lines (CCRF-CEM, MOLT-4, SR), CNS cell lines (SF-268, SF-539), Melanoma cell lines (LOX IMVI, M14, SK-MEL-5, UACC-257), Renal cell lines (A498, ACHN), lung cell lines (Hop-92), breast cell lines (MCF7, HS 578T), colon cell lines (COLO205), prostate cell lines (DU145, PC3) and ovarian cell lines (IGROV1, OVCAR-5).

5. The imidazothiazole-chalcone compound of formula 7a, 7e, 7f, 8f and 19e as claimed in claim 2, wherein the concentration of the compound used for in vitro activity against leukemia cell lines for $GI_{50}$ is in the range of 1.66 to 3.08, 1.55 to 2.23, 0.54 to 1.92, 0.49 to 2.33, 1.55 to 2.23 and 0.80 to 7.19 µm respectively at an exposure period of at least 48 hrs.

6. The imidazothiazole-chalcone compound of formula 7a, 7e, 7f, 8f and 19e as claimed in claim 2, wherein the concentration of the compound used for in vitro activity against lung cell lines for $GI_{50}$ is in the range of 0.24 to 3.70, 1.05 to 3.63, 1.65 to 7.00, 1.94 to 6.95 and 0.15 to 85.1 µm respectively at an exposure period of at least 48 hrs.

7. The imidazothiazole-chalcone compound of formula 7a, 7e, 7f, 8f and 19e as claimed in claim 2, wherein the concentration of the compound used for in vitro activity against colon cell lines for GI50 is in the range of 1.77 to 3.45, 2.11 to 2.99, 1.01 to 1.94, 1.40 to 4.56 and 2.92 to 9.93 µm respectively at an exposure period of at least 48 hrs.

8. The imidazothiazole-chalcone compound of formula 7a, 7e, 7f, 8f and 19e as claimed in claim 2, wherein the concentration of the compound used for in vitro activity against CNS cell lines for GI50 is in the range of 1.66 to 3.54 and 1.74 to 3.73, 1.38 to 2.67, 1.87 to 6.87 and 2.33 to 87.8 µm respectively at an exposure period of at least 48 hrs.

9. The imidazothiazole-chalcone compound of formula 7a, 7e, 7f, 8f and 19e as claimed in claim 2, wherein the concentration of the compound used for in vitro activity against melanoma cell lines for GI50 is in the range of 1.30 to 5.42, 1.82 to 8.27, 1.36 to 2.26, 0.60 to 8.48 and 0.51 to 7.07 µm respectively at an exposure period of at least 48 hrs.

10. The imidazothiazole-chalcone compound of formula 7a, 7e, 7f, 8f and 19e as claimed in claim 2, wherein the concentration of the compound used for in vitro activity against ovarian cell lines for GI50 is in the range of 0.21 to 4.05, 1.04 to 3.78, 1.86 to 3.08, 1.88 to 4.18, 2.28 to >100 µm respectively at an exposure period of at least 48 hrs.

11. The imidazothiazole-chalcone compound of formula 7a, 7e, 7f, 8f and 19e as claimed in claim 2, wherein the concentration of the compound used for in vitro activity against renal cell lines for GI50 is in the range of 1.12 to 5.04, 0.04 to 5.81, 1.56 to 2.30, 2.46 to 8.76 and 1.78 to 28.0 µm respectively, at an exposure period of at least 48 hrs.

12. The imidazothiazole-chalcone compound of formula 7a, 7e, 7f, 8f and 19e as claimed in claim 2, wherein the concentration of the compound used for in vitro activity against prostate cell lines for GI50 is in the range of 2.62 to 3.10, 2.45 to 3.43, 1.41 to 2.66, 1.64 to 5.39 and 2.41 to 7.52 µm respectively at an exposure period of at least 48 hrs.

13. The imidazothiazole-chalcone compound of formula 7a, 7e, 7f, 8f and 19e as claimed in claim 2, wherein the concentration of the compound used for in vitro activity against breast cell lines for IC50 is in the range of 1.90 to 3.46, 2.05 to 3.76, 1.25 to 2.92, 0.76 to 6.18 and 1.81 to 8.29 µm respectively at an exposure period of at least 48 hrs.

14. A process for preparation of Imidazothiazole-chalcone compound of formula as claimed in claim 1, comprising the steps of
providing imidazothiazole aldehyde of formula 5;

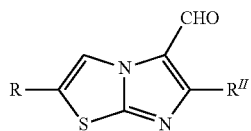

5 reacting the imidazothiazole aldehyde of formula 5 with the substituted ketone of formula 6 wherein R' represent trimethoxyphenyl, dimethoxyphenyl, dimethylphenyl, difluorophenyl, benzo[d][1,3]dioxolylnaphthalenyl, biphenyl, pyridinyl, indolyl, thiophenyl, pyrrolyl and furanyl in ethanol in the presence of 10-15% aqueous solution selected from the group consisting of sodium hydroxide, potassium hydroxide or barium hydroxide;

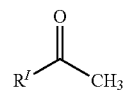

6 evaporating the organic solvent to obtain the residue which was dissolved in ethylacetate or water;
washing the organic layer with brine and evaporated;
purifying by column chromatography to obtain the desired products of formulae 7a-f to 18a-f and 19a-f to 30a-f wherein R represent hydrogen and methyl, R' represent trimethoxyphenyl, dimethoxyphenyl, dimethylphenyl, difluorophenyl, benzo[d][1,3]dioxolylnaphthalenyl, biphenyl, pyridinyl, indolyl, thiophenyl, pyrrolyl and furanyl and R" represent methoxyphenyl, chlorophenyl, methoxynitrophenyl, chloronitrophenyl, fluorophenyl and trifluoromethyl.

* * * * *